US010004684B2

(12) United States Patent
Whittle et al.

(10) Patent No.: US 10,004,684 B2
(45) Date of Patent: *Jun. 26, 2018

(54) PHARMACEUTICAL FORMULATIONS

(75) Inventors: Brian Whittle, Homsea (GB); Geoffrey Guy, Dorchester (GB)

(73) Assignee: GW Pharma Limited, Cambridge (GB)

(*) Notice: Subject to any disclaimer, the term of this patent is extended or adjusted under 35 U.S.C. 154(b) by 2058 days.

This patent is subject to a terminal disclaimer.

(21) Appl. No.: 10/468,041

(22) PCT Filed: Feb. 14, 2002

(86) PCT No.: PCT/GB02/00620
§ 371 (c)(1),
(2), (4) Date: Apr. 22, 2004

(87) PCT Pub. No.: WO02/064109
PCT Pub. Date: Aug. 22, 2002

(65) Prior Publication Data
US 2004/0192760 A1 Sep. 30, 2004

Related U.S. Application Data

(63) Continuation-in-part of application No. 09/951,022, filed on Sep. 12, 2001, now Pat. No. 7,025,992, and a continuation-in-part of application No. 09/827,158, filed on Apr. 5, 2001, now Pat. No. 6,730,330.

(60) Provisional application No. 60/280,044, filed on Mar. 30, 2001.

(30) Foreign Application Priority Data

Feb. 14, 2001 (GB) .................................. 0103638.3
May 11, 2001 (GB) .................................. 0111597.1
Sep. 7, 2001 (GB) .................................. 0121715.7

(51) Int. Cl.
A61K 31/353 (2006.01)
A61K 9/00 (2006.01)
A61K 9/107 (2006.01)
A61K 9/12 (2006.01)
A61K 9/24 (2006.01)

(52) U.S. Cl.
CPC ............ A61K 9/0031 (2013.01); A61K 9/006 (2013.01); A61K 9/0073 (2013.01); A61K 9/0056 (2013.01); A61K 9/1075 (2013.01); A61K 9/122 (2013.01); A61K 9/209 (2013.01)

(58) Field of Classification Search
CPC ........................ A61K 31/353; A61K 9/0031
See application file for complete search history.

(56) References Cited

U.S. PATENT DOCUMENTS 3,428,728 A 2/1969 Lowey
3,560,625 A 2/1971 Costello et al.
4,279,824 A * 7/1981 McKinney .................. 549/390
4,824,570 A * 4/1989 Bethuel et al. ............. 210/511
5,047,230 A 9/1991 Nagy et al.
5,462,749 A 10/1995 Rencher
5,514,673 A 5/1996 Heckenmuller et al.
5,540,934 A 7/1996 Touitou
6,113,940 A 9/2000 Brooke et al.
6,328,992 B1 * 12/2001 Brooke et al. ............... 424/449
6,730,330 B2 5/2004 Whittle et al.
6,946,150 B2 9/2005 Whittle
7,025,992 B2 4/2006 Whittle et al.
7,709,536 B2 5/2010 Whittle
8,211,946 B2 7/2012 Whittle
8,603,515 B2 12/2013 Whittle
9,029,423 B2 5/2015 Whittle
9,421,187 B2 8/2016 Izzo et al.
2002/0111377 A1 8/2002 Stinchcomb
2010/0286098 A1 11/2010 Robson et al.
2014/0296351 A1 10/2014 Whittle
2014/0343136 A1 11/2014 Izzo et al.
2016/0068321 A1 3/2016 Whittle

FOREIGN PATENT DOCUMENTS

CA 2 322 549 A1 3/2002
EP 2 286 793 A2 2/2011
GB 2 285 921 A 8/1995
GB 2 361 869 A 11/2001

(Continued)

OTHER PUBLICATIONS

Williamson et al 'Cannabinoids in Clinical Practice' Drugs, 60(6), p. 1303-1314, 2000.*
Gershanik, T. et al., "Positively-charged self-emulsifying oily formulation for improving oral bioavailability of progesterone," Proc. $1^{st}$ World Meet. Pharm., Pharm. Technol. 1995; 639-40.
Gershanik, T. et al., "Cyclosporine A absorption enhancement in perfused Rat intestine by positively charged self-emulsifying oil formulations," Proc. $26^{th}$ Int. Symp. Controlled Release Bioact. Mater. 1999; 913-914.
Hiltunen, A.J. et al., "Behaviour in rats maintained by low differential reinforcement rate: effects of delta-1 tetrahydrocannabinol, cannabinol and cannabidiol, alone and in combination," Neuropharmacology 1989; 28(2):183-189.
Murphy, L.L. et al., "Effects of Delta-9-Tetrahydrocannabinol, Cannabinol and Cannabidiol, Alone and in Combinations, on Luteinizing Hormone and Prolactin Release and on Hypothalamic Neurotransmitters in the Male Rat," Neuroendocrinology 1990; 52:316-321.

(Continued)

Primary Examiner — Craig D Ricci
Assistant Examiner — Christopher R Stone
(74) Attorney, Agent, or Firm — Wolf, Greenfield & Sacks, P.C.

(57) ABSTRACT

The invention relates to pharmaceutical formulations for use in the administration of lipophilic medicaments via mucosal surfaces. In particular the invention provides pharmaceutical formulations for use in administration of a lipophilic medicament via a mucosal surface which upon hydration form an emulsion containing the lipophilic medicament which is capable of adhering to a mucosal surface and allowing controlled release of the medicament. The invention further provides pharmaceutical formulations which contain, as active ingredients, specific combinations of cannabinoids in pre-defined ratios.

34 Claims, 5 Drawing Sheets

(56) References Cited

FOREIGN PATENT DOCUMENTS

| | | | |
|---|---|---|---|
| GB | 2 368 098 A | | 4/2002 |
| GB | 2 377 633 A | | 1/2003 |
| GB | 2 368 061 B | | 5/2005 |
| WO | WO 95/05163 A1 | | 2/1995 |
| WO | WO 95/25504 A1 | | 9/1995 |
| WO | WO 95/34286 A1 | | 12/1995 |
| WO | WO 99/16417 A1 | | 4/1999 |
| WO | WO 99/32107 A1 | | 7/1999 |
| WO | WO 99/52524 A1 | | 10/1999 |
| WO | WO 00/24362 A2 | | 5/2000 |
| WO | WO 00/25127 A1 | | 5/2000 |
| WO | WO 00/56303 A2 | | 9/2000 |
| WO | WO 01/03668 | * 1/2001 | ............ A61K 9/127 |
| WO | WO 01/66089 A2 | | 9/2001 |
| WO | WO 02/032420 A1 | | 4/2002 |
| WO | WO 02/064109 A2 | | 8/2002 |
| WO | WO 02/069993 A1 | | 9/2002 |

OTHER PUBLICATIONS

Whittle, B.A. et al., "Yields and Consistency of Cannabinoids in Cannabis Species," 3$^{rd}$ International Symposium Bioresource Hemp & Other Fine Fibre Crops, Wolfsburg Sep. 13-16, 2000; Retrieved from http://www.nova-institute.de/bioresource-hemp/vortraege/watson.htm.

Williams, E.M. et al., "Cannabinoids in Clinical Practice," *Drugs* Dec. 2000; 60(6):1303-1314.

Zuardi, A.W. et al., "Effects on Variable-Interval Performance in Rats of Delta-1 Tetrahydrocannabinol and Cannabidiol, Separately and in Combination," *Brazilian J. Med. Biol. Res.* 1983; 16(2):141-146.

Guy, G.W. et al., "Pilot Study: the effects of cannabis based medicine on cognitive performance," HSE Books, 2000; pp. 3 and 8.

The United Kingdom Parliament, Select Committee on Science and Technology Ninth Report (1998) at http://www.parliament.the-stationery-office.co.uk/pa/ld199798/ldselect/ldsctech/151/15101.htm.

The United Kingdom Parliament, Select Committee on Science and Technology Second Report (Mar. 14, 2001) at http://www.publications.parliament.uk/pa/ld200001/ldselect/ldsctech/50/5001.htm.

Frischknecht, H.R. et al., "Behavioral effects of hashish in mice," *Psychopharmacology* 1980; 70:155-161.

Gorter, R.W., "Cancer cachexia and cannabinoids," *Research in Complementary Medicine* 1999; 6 (supp 3): 21-22.

Guy, G.W. et al., "A phase one study of sublingual cannabis-based medicine extract," *J. Pharm. Pharmacol.* 2000; 52 (supp):294.

Hollister, L.E. et al., "Interactions in man of delta-9-tetrahydrocannabinol. II. Cannabinol and cannabidiol," *Clinical Pharmacology and Therapeutics* 1975; 18:80-83.

Karniol, I.G. et al., "Cannabidiol Interferes with the Effects of $\Delta^9$-Tetrahydrocannabinol in Man," *European Journal of Pharmacology* 1974; 28:172-177.

Tashkin, D. P. et al., "Bronchial Effects of Aerosolized $\Delta^9$-Tetrahydrocannabinol in Healthy and Asthmatic Subjects," *American Review of Respiratory Disease* 1977; 115:57-65.

Vachon, L. et al., "Airways response to Micro-Aerosolized Delta-9-$\Delta^9$-Tetrahydrocannabinol," *Chest* 1976; 70:444.

Williams, S.J. et al., "Bronchodilator effect of $\Delta^1$-tetrahydrocannabinol administered by aerosol to asthmatic patients," *Thorax* 1976; 31:720-723.

Zuardi, A.W. et al., "Action of Cannabidiol on the Anxiety and Other Effects Produced by $\Delta^9$-THC in Normal Subjects," *Psychopharmacology* 1982; 76:245-250.

International Search Report for PCT/GB2002/000620 dated Nov. 12, 2002.

International Preliminary Examination Report for PCT/GB2002/000620 dated Jun. 3, 2003.

Notice of Opposition for EP02712063.3 dated Sep. 19, 2014.

[No Author Listed] Product Information for Nitrolingual Pumpspray. Oct. 1, 2008.

Alhanaty et al., Osmotic fragility of liposomes as affected by antihelmolytic compounds. Biochim Biophys Acta. Feb. 26, 1974;339(1):146-55.

Fetterman et al., Constituents of *Cannabis sativa* L. I. Propyl homologs of cannabinoids from an Indian variant. J Pharm Sci. Sep. 1972;61(9):1476-7.

Garrett et al., Physiochemical properties, solubility, and protein binding of delta9-tetrahydrocannabinol. J Pharm Sci. Jul. 1974;63(7):1056-64.

Guy et al., Contract Research Report 300: Pilot Study: The Effect of Cannabis Based Medicine on Cognitive Performance. Health and Safety Executive. Nov. 2000: 62 pages.

Handbook of Pharmaceutical Excipients. 2000, 3$^{rd}$ Edition. American Pharmaceutical Association, Washington DC. Kibbe, ed. pp. 7-9, 220-222, 412-415, 442-444.

Simamora et al., Solubilization of rapamycin. Int J Pharm. Feb. 1, 2001;213(1-2):25-9.

Touitou et al., Transdermal Delivery of Tetrahydrocannabinol. Int J of Pharmaceutics. 1988;43:9-15.

U.S. Appl. No. 10/218,989, filed Aug. 14, 2002, Granted, U.S. Pat. No. 6,946,150.

U.S. Appl. No. 11/229,052, filed Sep. 16, 2005, Granted, U.S. Pat. No. 7,709,536.

U.S. Appl. No. 12/704,729, filed Feb. 12, 2010, Granted, U.S. Pat. No. 8,211,946.

U.S. Appl. No. 13/486,227, filed Jun. 1, 2012, Granted, U.S. Pat. No. 8,603,515.

U.S. Appl. No. 14/074,067, filed Nov. 7, 2013, Published, 2014-0296351.

U.S. Appl. No. 12/667,561, filed Jul. 21, 2010, Published, 2010-0286098.

U.S. Appl. No. 14/359,192, filed May 19, 2014, Published, 2014-0343136.

PCT/GB2002/000620, dated Nov. 12, 2002, International Search Report.

PCT/GB2002/000620, dated Jun. 3, 2003, International Preliminary Examination Report.

EP02712063.3, dated Sep. 19, 2014, Notice of Opposition.

* cited by examiner

FIG. 8

Medicinal Cannabis (High-THC or High-CBD)

↓

Chopping to predominantly 2 to 3mm

↓

Heating at 100 to 150°C for sufficient time to decarboxylate acid form of cannabinoids to produce neutral cannabinoids

↓

Extraction with a specified volume of liquid carbon dioxide over 6 to 8 hours

↓

Removal of $CO_2$ by depressurisation to recover crude extract

↓

"Winterisation"-Dissolution of crude extract in ethanol Ph. Eur. followed by chilling solution (-20°C/48 hrs) to precipitate unwanted waxes

↓

Removal of unwanted waxy material by cold filtration

↓

Removal of ethanol from the filtrate by thin film evaporation under reduced pressure

PHARMACEUTICAL FORMULATIONS

RELATED APPLICATIONS

This application is a national stage filing under 35 U.S.C. § 371 of PCT International application PCT/GB02/00620, filed Feb. 14, 2002, which was published under PCT Article 21(2) in English, which is a continuation in part of U.S. patent application Ser. No. 09/951,022, entitled PHARMACEUTICAL FORMULATIONS, filed Sep. 12, 2001, which is a continuation-in-part of U.S. patent application Ser. No. 09/827,158, entitled PHARMACEUTICAL FORMULATIONS, filed Apr. 5, 2001, which claims priority under 35 U.S.C. § 119 from United States provisional application entitled PHARMACEUTICAL FORMULATIONS, Ser. No. 60/280,044, filed Mar. 30, 2001, the entire contents of which applications are incorporated in their entirety herein by reference.

The invention relates to pharmaceutical formulations for use in the administration of medicaments, in particular lipophilic medicaments, via mucosal surfaces.

Medicaments taken by mouth and swallowed are absorbed first into the blood perfusing the gastrointestinal tract. The venous drainage from the GI tract is into the blood perfusing the liver. This means that medicaments absorbed from the lumen of gastrointestinal tract are immediately presented to the liver—the major detoxifying organ of the body. In addition to protecting the organism from ingested toxins, the liver also metabolises medicaments which are treated in the same way. Blood from the liver then returns to the left side of the heart via the hepatic portal vein and reaches the rest of the systemic circulation. This first pass through the liver may result in the removal of a substantial proportion of an ingested medicament. The first pass effect is more pronounced for some drugs than others; in the case of cannabinoids more than 90% of an ingested dose is removed during the first pass.

Certain areas of the alimentary canal have a venous drainage which does not involve a first pass through the liver. These areas (the mucous membrane of the buccal cavity, under the tongue and the nasopharynx, and also the distal rectum) drain directly into the left side of the heart. The avoidance of the first pass effect is the rationale for the use of buccal, nasal and sublingual formations, and also suppositories. Each of these types of formulation has advantages and disadvantages, as follows:

Suppositories are subject to hygiene and patient compliance restrictions.

Formulations intended for administration to the nasal mucosae may cause pain or reflex sneezing, and in extreme cases cause irritation and damage to the nasal mucosae.

Sublingual formulations may stimulate the flow of saliva and it is difficult for patients to avoid swallowing when substantial amounts of saliva are produced. Buccal formulations may be subject to the same limitations.

Both sublingual and buccal formulations depend on the efficient transfer of medicament from a hydrophilic vehicle to the mucous membrane of the sublingual or buccal mucosae. Transfer of medicament through the interstices between or through epithelial cells is governed principally by the lipid solubility of the medicament. Where a drug is water insoluble this is a further barrier to absorption from the sublingual area. There are therefore physical and biological limitations on the therapeutic usefulness of lipophilic medicaments, such as for example cannabis and cannabinoids, given by mouth and swallowed.

The present invention relates to formulations which are particularly suitable for use for administration of lipophilic medicaments via a mucosal surface such as, for example, the sublingual mucosa or the buccal mucosa.

Therefore, in accordance with a first aspect of the invention there is provided a pharmaceutical formulation for use in administration of a lipophilic medicament via a mucosal surface comprising at least one lipophilic medicament and at least one self emulsifying agent, wherein upon hydration the formulation forms an emulsion containing the lipophilic medicament which is capable of adhering to a mucosal surface and allowing controlled release of the medicament.

By direct experiment it has been shown that lipophilic medicaments can be effectively brought into intimate contact with the absorptive mucous membrane when they are formulated into a self-emulsifying formulation.

In the context of the present invention the following terms will be understood to have the following meanings:

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion. In the case of the spray formulations disclosed herein, self-emulsification occurs on contact with the alternative phase (saliva).

A "primary" (self) emulsifier is one whose primary function is as a (self) emulsifier.

A secondary (self) emulsifier is one whose secondary function is as a (self) emulsifier. The secondary (self) emulsifier may have another function, e.g. as a solubiliser or viscosifying agent.

Generally a self-emulsifying agent will be a soluble soap, a salt or a sulphated alcohol, especially a non-ionic surfactant or a quaternary compound. These are often known as self-emulsifying grades (SE grade), e.g. SE grade glyceryl mono oleate, and SE grade glyceryl monostearate.

The "Hydrophilic Lipophilic Balance" (HLB) system, the balance between the hydrophilic and lipophilic moieties of a surface-active molecule, is used as a basis for rational means of selecting and classifying emulsifying agents. In the HLB system each emulsifying agent is assigned a number between 1 and 20 (see Pharmaceutical Codex). Emulsifying agents with HLB values of between 3 and 6 are lipophilic and form water-in-oil emulsions, while values of 8 to 18 indicate predominantly hydrophilic characteristics and the formation of oil-in-water emulsions. The preferred emulsifying agents for use in the present invention generally exhibit HLB values of between 8 and 18.

Surprisingly, formulations according to the invention do not produce reflex salivation as salivary secretion is attracted into the dose unit, and forms in situ an emulsified mass. Further, the mass so formed adheres to and forms a layer on the mucosal surface, typically the buccal and/or sublingual mucosae, and thereby provides a controlled release formulation.

In a preferred embodiment the formulation according to the invention is not a propellant-driven aerosol or liquid spray.

The preparation of liquid formulations for oropharangeal delivery of cannabinoids poses a number of problems. First, it is necessary to deliver at least 1.0 mg, more preferably at least 2.5 mg and even more preferably at least 5 mg of cannabinoids per 0.1 ml of liquid formulation to achieve a therapeutic effect in a unit dose. In this regard a patient may require up to 120 mg cannabinoid/day, on average around 40 mg/day to be taken in a maximum of six doses.

In the case of a sublingual or buccal delivery, this means delivering this quantity of the active ingredient in an amount of formulation which will not be swallowed by the patient, if the active ingredient is to be absorbed transmucosally.

Whilst such amounts can be achieved by dissolving the cannabinoid in ethanol as the solvent, high concentrations of ethanol provoke a stinging sensation and are beyond the limit of tolerability.

There is thus a need to use a co-solvent in order to reduce the amount of ethanol, whilst still enabling sufficient quantities of cannabinoid to be solubilised.

The applicant has discovered that the choice of co-solvent is limited and should be selected from either:
i) a co-solvent which acts as a solubility enhancer, or
ii) a co-solvent which has a solubilizing effect sufficient to allow enough cannabinoid to be solubilised in a unit dose, namely at least 1.0 mg/0.1 ml of formulation, and which allows the amount of solvent present to be reduced to a level which is within the limits of patient tolerability.

Particularly suitable co-solvents with reference to i) above are polyoxyethylene castor oil derivatives, particularly cremophor.

Particularly suitable co-solvents with reference to ii) above are propylene glycol and glycerol.

Most preferably the formulation according to the invention is a solid dosage form such as, for example, a solid gel (e.g. a gel which is flexible but which has dimensional stability), pastille, compressed tablet, lozenge, capsule etc, or a gel-spray.

The dosage units are preferably homogeneous in composition, but also included within the scope of the invention are multi-layered dosage units formed from layers of differing composition, for example two-layered tablets and gels, as illustrated in the accompanying Examples, in which the different layers contain different active ingredients and/or exhibit different release characteristics.

Gel-spray formulations may also include one or more solvents and optionally also one or more co-solvents.

Suitable solvents for use in gel-spray formulations include ethanol. Suitable co-solvents agents include glycerol.

Gel-sprays can be distinguished from "liquid" formulations on the basis of viscosity. Gel-sprays are generally more viscous than simple ethanolic solutions. Typically, the viscosity of a gel-spray will be in the range of 10,000-20,000 centipoises.

Suitable self-emulsifying agents which may be included into the formulations of the invention include, inter alia, those substances which are indicated as primary and secondary emulsifiers in Table 2. Preferred self-emulsifying agents include glyceryl mono-oleate and glyceryl monostearate (particularly the self-emulsifying grade). With glyceryl mono-oleate and glyceryl monostearate (other than self-emulsifying grades) it is usual to add, for example, a small amount of alkali in order to produce a "self-emulsifying" agent.

For solid dosage formulations the total amount of self-emulsifying agent(s) included in the formulation is preferably at least 5% w/w, more preferably at least 10% w/w of the formulation.

For gel-spray formulations the total amount of self-emulsifying agent(s) included in the formulation is preferably at least 2% w/w, more preferably at least 5% w/w of the formulation.

The total amount of self-emulsifier generally varies in proportion to the total amount of active ingredient (lipophilic medicament) included in the formulation; the greater the amount of active ingredient, the greater the amount of self-emulsifying agents. The formulations according to the invention are intended to accommodate amounts greater than 1% of the active ingredient. Most preferably the relative proportions of self-emulsifying agent to active ingredient should be between 1% self-emulsifier per 10% active and 1% self-emulsifier per 5% active. The total amount of self-emulsifying agents may also be varied in order to produce a formulation with the desired dissolution/disintegration characteristics in the mouth, since it is observed by experiment that increasing the amount of self-emulsifying agent has the effect of increasing dissolution/disintegration time (see Example 14).

The formulation may further comprise one or more viscolising agents (agents which increase viscosity). Suitable viscolising agents include those listed in Table 2 below.

Preferably the viscolising agent(s) is/are not block copolymers of oxyethylene and oxypropylene. More preferably the viscolising agents are non nonionic surfactants. In the latter case these formulations may contain self-emulsifying agents which are nonionic surfactants, but additionally contain at least one viscolising agent which is not a nonionic surfactant.

In a preferred embodiment, the formulation may comprise at least one viscolising agent which is solubilised by the action of an enzyme present in saliva. Examples of such a viscolising agents include starches, for example pre-gelatinised starch, which are solubilised by the action of salivary amylase.

The inclusion of viscolising agents which are susceptible to enzymatic degradation may result in the formation of an in situ mass comprising the lipophilic medicament which has the characteristics for optimising absorption from the buccal cavity and sublingual mucosae. This has the advantage of allowing solid gels to be rapidly dissolved (in, for example, a matter of minutes).

A wide variety of hydrophilic viscolising agents have been used in pharmaceutical preparations and it is known that gels formed by hydration of these substances may have a surface electrical charge. Table 2 lists some agents (but without restriction to the scope of the invention), which have this property, and indicates those that have received regulatory approval in preparations intended for oral administration. The table also indicates the sign of the surface charge, where it is known.

In a preferred embodiment the formulation may comprise at least one viscolising agent that when hydrated forms a gel having a positive surface charge and at least one viscolising agent that when hydrated forms a gel having a negative surface charge. In the most preferred embodiment the formulation may comprise at least one viscolising agent that when hydrated forms a gel having a positive surface charge which is a gelatin or glycogelatin and at least one viscolising agent that when hydrated forms a gel having a negative surface charge which is a starch, pre-gelatinised starch, acacia or polydextrose.

Surprisingly it has been found that by selective admixture of materials producing gels of opposing electrical charge it is possible to modify the solubility characteristics of the resulting mixture and to control the rate of release of medicament from this formulation, in particular by solubilisation of at least one component by the amylolytic enzyme present in saliva.

It is possible to modify the physical properties of the dosage form by varying the total amount of viscolising agents and also by varying the proportion of the materials forming gels of positive and negative surface charge. In general, increasing the relative amount of positively charged viscolising agent (e.g. gelatin or glycogelatin) has the effect of slowing down dissolution/dispersion in the mouth, whereas increasing the relative amount of negatively charged viscolising agent (e.g. starch or pre-gelatinised starch) has the effect of speeding up dissolution/dispersion in the mouth (see Example 14). The proportion of positive and negatively charged viscolising agents included in the formulation may therefore be varied to produce a dosage form which exhibits the desired release characteristics.

For solid dosage forms the total amount of viscolising agent(s) (including any gelling agents) included in the formulation will preferably be greater than 60% w/w of the formulation.

For gel-spray dosage forms the total amount of viscolising agent(s) included in the formulation will preferably be greater than 1% w/w of the formulation, most preferably greater than 2% w/w of the formulation. Preferred viscolising agents for inclusion into gel-spray formulations include, for example, carboxymethyl cellulose.

Further excipients may be included in the formulations according to the invention as appropriate. For example, the formulations may include one or more antioxidants. Preferred antioxidants include α-tocopherol, ascorbyl palmitate, butylated hydroxy anisole (BHA) etc. The formulation may also include one or more colouring agents. Suitable colouring agents include, for example, curcumin or chlorophylls.

The accompanying examples illustrate formulations which optimise the absorption of strongly lipophilic medicaments through the mucosae of the buccal and sublingual epithelia and result in the required pharmacokinetic profile for optimum therapeutic action. The formulations contain at least one self-emulsifying component that in contact with saliva forms a viscous emulsion which adheres, reversibly, to the mucous membrane, without causing irritation or damage, or stimulating excessive salivation. When the dosage form is introduced into the mandibular or maxillary fossae, or placed under the tongue it hydrates and adheres to the mucosae. The hydrated, emulsified mass so formed remains in contact with a large area of the buccal and sublingual mucosae, and releases medicament over a period of time.

The controlled release characteristics of the formulation, i.e. disintegration time, may be varied by varying the relative amounts of excipients included into the formulation, in particular the amounts of self-emulsifying agents and viscolising agents, if present. The disintegration characteristics may therefore be varied to suit the type of lipophilic medicament included in the formulation, since it is desirable that the formulation remain in contact with the mucosal surface for a period of time sufficient to allow substantially all of the lipophilic medicament to be absorbed through the mucosal surface into the systemic circulation. The rate at which the lipophilic medicament is absorbed is obviously dependent on the nature of the medicament. In the case of cannabinoids, significant absorption through the buccal or sublingual mucosa is achieved in a period of about 10 minutes. It is therefore desirable that any formulation for delivery of cannabinoids remain substantially intact and in contact with the mucosal surface for at least this time.

Most preferably formulations according to the invention will disintegrate completely within a period of from 0.1-60 minutes, more preferably within 0.5-15 minutes, but formulations within the scope of the invention have been produced in which disintegration time is at least 90 minutes.

Table 1 lists examples of medicaments which can be included in the formulations according to the invention. Classes of compound are indicated in bold. Examples of compounds are intended to be illustrative rather than limiting to the invention. The person skilled in the art will appreciate that compounds having a unit dose less than 10 mg are most conveniently given in the form of small tablets as described in Example 6. Compounds where the unit dose is greater are most conveniently included in the gel formulations which can accommodate higher unit doses of medicament.

TABLE 1

| CLASS OF MEDICAMENT | EXAMPLE OF MEDICAMENT |
| --- | --- |
| Alkaloid-rich extracts of *Belladonna atropa* | Hyoscine<br>Hyoscymine<br>Atropine |
| Alkaloid-rich extracts of Gallanthus spp. | |
| Alkaloid-rich extracts of Narcissus spp. | |
| Alkaloid-rich extracts of opium | Morphine<br>Codeine<br>Diamorphine |
| Alkaloid-rich extracts of Pilocarpine | Pilocarpine salycilate |
| Anti-asthmatics | Terbutaline |
| Antibacterials | |
| Antifungals | Fluconazole |
| Anti-inflammatory agents | Benzidamine<br>Pyroxicam |
| Antivirals | Acyclovir<br>Zidovudine |
| Beclomethasone | |
| Cannabinoid-rich fractions of *Cannabis sativa* and *Cannabis indica*, and chemovars derived from them | |
| Cannabinoids | $\Delta^{-9}$ Tetrahydrocannabinol (THC)<br>Cannabidiol (CBD)<br>Cannabinol (CBN) |
| Cannabinoid-rich fractions containing cannabinoids other than THC, CBD or CBN as the most abundant component | |
| Cardiovascular Agents | Nifedipine<br>Diltiazem<br>Verapamil |
| Centrally acting analgesics | Butorphenol<br>Buprenorphine<br>Fentanyl |
| Antiangina agents | Nitrates |
| Fluticasone proprionate | |
| Polyunsaturated fatty acid triglycerides | n-3 and n-6 PUFAs<br>Acylglycerols |
| Sympathomimetic amines | Salbutamol |

Table 2 lists pharmaceutically acceptable excipients and types of excipient which can be included (without limitation of the invention) to give a suitable degree of viscosity when the dose unit is placed in contact with saliva. The dosage form may be formed by fusion or compression into a mould sealable to exclude light and air.

Table 2 lists classes of compound and examples of agents which can be used to produce emulsification, mucoadhesion and an increase in viscosity. The designation as primary (1°) or secondary (2°) emulsifier is for convenience. Many of the agents can be used alone or in combination to fulfill the role of primary or secondary emulsifier.

TABLE 2

| Compound Class/Example | Preferred Quantity % w/w | Surface Charge (where known) | Regulatory Approval | Comments |
|---|---|---|---|---|
| Acacia | | Negative | M | Forms a viscous coacervate with positively charged gels such as gelatin |
| Alcohols | | | | |
| Cetostearyl | 1-20 | | F, M | 2° emulsifier |
| Cetyl | 1-15 | | | 2° emulsifier |
| Anionic emulsifying wax | 3-30 | | M | 1° self emulsifier |
| Cellulose, hydroxypropyl | 5-35 | | G, F, M, R | 2° emulsifier, stabiliser, viscoliser |
| Diethanolamine (DEA) | 1-10 | | M, F, R | 1° self emulsifier |
| Gelatin | 40-70 | Positive | F, M | Gelling agent |
| Glyceryl monoleate | 1-30 | | G, F, R | 1° self emulsifier, solubiliser |
| Glyceryl monostearate | 2-20 | | G, M, F, R | 1° self emulsifier, solubiliser, tablet lubricant |
| Lecithin | 2-15 | | G, M, F, R | 2° emulsifier |
| Medium Chain Triglycerides | 1-10 | | G, R | 2° emulsifier, solvent |
| Methylcellulose | 1-5 | | G, M, F, R | 2° emulsifier, viscoliser |
| Nonionic emulsifying wax | 5-25 | | M, R | 1° emulsifier, viscoliser |
| Poloxamer | 2-10 | | M, F, R | 2° emulsifier, viscoliser |
| Polydextrose | | Negative | | Viscoliser |
| Polyethoxylated Castor Oil | 1-10 | | M, F, R | 1° self emulsifier, solubiliser, stabiliser |
| Polyoxyethylene alkyl ethers | 10-20 | | M, R | 1° self emulsifier, solubiliser |
| Polyoxyethylene ethers (Macrogols) | 1-15 | | M, R | 1° self emulsifier, solubiliser, wetting agent |
| Polyoxyethylene fatty acid esters (polysorbates) | 0.5-10 | | G, M, F, R | 1° self emulsifier, solubiliser |
| Polyoxyethelene stearates | 0.5-10 | | M, F, R | 2° emulsifier, solubiliser |
| Pregelatinised starch | 1-20 | Negative | G, F, R | Coacervates with gelatin, viscolisers |
| Propylene glycol alginate | 1-5 | | G, M, F, R | 2° emulsifier, viscoliser |
| Sodium lauryl sulfate | 0.5-2.5 | | G, M, F, R | 1° self emulsifier |
| Sorbitan esters (sorbitan fatty acid esters) | 0.1-15 | | Food, M, F, R | 1° self emulsifier, solubiliser |
| Starch | 2-15 | Negative | G, M, F, R | Viscoliser, tablet diluent, disintegrant |
| Tri-sodium citrate | 0.3-4 | | G, M, F, R | 2° emulsifier, pH modifier, sequestering agent |

M—Monograph in major pharmacopoeias
F—Accepted in FDA Inactive Ingredients Guide
R—Included in parenteral medicines, licensed in the UK or Europe
G—Generally Regarded as Safe In accordance with a second aspect of the invention there is provided a pharmaceutical formulation for use in administration of a lipophilic medicament via a mucosal surface, the formulation comprising at least one lipophilic medicament, at least one solvent, at least one co-solvent, which is preferably also a solubilising agent, and at least one self emulsifying agent, wherein upon hydration the formulation forms an emulsion containing the lipophilic medicament which is capable of adhering to a mucosal surface and allowing controlled release of the medicament, characterised in that the total amount of solvent and co-solvent present in the formulation is greater than 55% w/w of the formulation.

In a preferred embodiment this formulation may be a liquid dosage form, for example an aerosol, liquid spray or drops. The technical principle of delivery of a lipophilic active ingredient to a mucosal surface in a self-emulsifying formulation which adheres to the mucosa for sufficient time to allow absorption of the lipophilic medicament can thus be extended to liquid dosage forms. A preferred embodiment is a liquid formulation administered via a pump-action spray.

A pump-action spray is found to be particularly beneficial when it comes to delivering cannabinoids. Indeed previously people have considered pump-action sprays to be unsuitable for drug delivery and people have focussed their attention on solvent systems including a propellant.

Whilst it has been recognised that there are disadvantages with such systems, including the speed of delivery, those skilled in the art have tried to address this by slowing the propellant by altering the nozzle. The applicants have found that by using a pump spray with their formulations they are able to produce a spray in which the particles have a mean aerodynamic particle size of between 15 and 45 microns, more particularly between 20 and 40 microns and an average of about 33 microns. These contrast with particles having a mean aerodynamic particle size of between 5 and 10 microns when delivered using a pressurised system.

In fact, comparative tests by the applicant have shown such a pump-action spray system to have advantages in being able to deliver the active components to a larger surface area within the target area. This is illustrated with reference to the accompanying Example 12.

The variation in particle distribution and sprayed area has been demonstrated by direct experiment. A formulation as described in the accompanying Example 12 was filled into a pump action spray assembly (Valois vial type VP7100 actuated). The same formulation was filled into a pressurised container powered by HFA 134a.

Both containers were discharged at a distance of 50 ml from a sheet of thin paper held at right angles to the direction of travel of the jet. The pattern of spray produced in both cases by discharge of 100 μl was then visualised against the light. In both cases the pattern of discharge was circular and measurements were as follows:

|                   | Mean Diameter (mm) | Mean Area (mm$^2$) |
|-------------------|--------------------|--------------------|
| Pump Action Spray | 23                 | 425.5              |
| Pressurised Spray | 16                 | 201.1              |

The pressurised spray produced pooling of liquid at the centre of the area. The pump action spray gave a more even pattern of pooling and less "bounce back". There was also a significantly greater area covered by the pump action spray. The conditions under which this test was carried out are relevant to the in-practice use of the device. A wider area of buccal mucosa can be reached by the PAS compared with the pressurised spray.

In a preferred embodiment the total amount of solvent and co-solvent present in the formulation, absent of propellant, is greater than 65% w/w, more preferably greater than 70% w/w, more preferably greater than 75% w/w, more preferably greater than 80% w/w, more preferably greater than 85% w/w of the formulation. Most preferably the total amount of solvent and co-solvent present in the formulation is in the range from 80% w/w to 95% w/w of the formulation.

Preferred solvents for use in this formulation are lower alkyl ($C_1$-$C_4$) alcohols, most preferably ethanol.

Preferred co-solvents for use in this formulation include propylene glycol, glycerol, macrogols and also co-solvents which are also solubilising agents, of which preferred examples are polyoxy hydrogenated castor oils. It is within the scope of the invention for the "solubilising agent" and "self-emulsifying agent" included in the formulation to be the same chemical substance.

In the content of this application the term "solubilising agent" refers to a substance which preferably increases solubility of the active ingredient (i.e. the lipophilic medicament) within the formulation. In the formulation according to this second aspect of the invention a solubilising agent may be included to overcome the problem of improving solubility of the active ingredient (lipophilic medicament) in formulations containing a limited amount of ethanol. Thus the addition of a solubilising agent generally has the effect of increasing the amount of active ingredient which can be incorporated into the formulation, whilst maintaining patient tolerability.

The advantage of including a co-solvent is particularly well illustrated with reference to formulations wherein the lipophilic medicament comprises one or more cannabinoids. Cannabinoid generally have limited solubility in many solvents and this places a limitation on the amount of cannabinoids which may be incorporated into pharmaceutical formulations. For example aerosol sprays containing ethanol plus a propellant could only stabilise 0.7 mg of THC per 0.1 ml of liquid formulation. As a consequence, multiple applications of these formulations must be administered to the patient in order to achieve a pharmaceutically significant dose of the active cannabinoid. The addition of a co-solvent which is a better Solubiliser than standard propellants, for example propylene glycol, glycerol, a macrogol or a polyoxy hydrogenated castor oil, as taught by the present invention, enables incorporation of a far greater about of active cannabinoids which in turn means that it is possible to administer a pharmaceutically relevant dose of cannabinoid in a single application of the formulation.

In a preferred embodiment the formulation contains ethanol as a solvent and propylene glycol as co-solvent. In this embodiment the ratio of ethanol to propylene glycol present in the formulation is preferably in the range from 4:1 to 1:4 and is most preferably 1:1.

In a further preferred embodiment the formulation contains ethanol as a solvent and a polyoxy hydrogenated castor oil (most preferably cremophor RH40) as a co-solvent/solubilising agent. In this embodiment the amount of polyoxy hydrogenated castor oil present in the formulation is preferably between 5% and 55% w/w, more preferably between 20% and 40% w/w and most preferably 30% w/w of the total amount of polyoxy hydrogenated castor oil plus ethanol (% w/w) present in the formulation, and is more preferably of the total amount of polyoxy hydrogenated castor oil plus ethanol (% w/w) present in the formulation. The total amount of polyoxy hydrogenated castor oil plus ethanol may be up to 97% w/w of the formulation.

Suitable self-emulsifying agents which may be included in this formulation are those listed in Table 2, and described above in connection with the first aspect of the invention. Most preferred are glyceryl mono-oleate and glyceryl monostearate (preferably the self-emulsifying grade).

In this formulation the total amount of self-emulsifying agents is preferably greater than 1% w/w of the formulation.

Other excipients may be included in the formulation, such as antioxidants, flavourings etc., as described above. Most preferably the formulation does not contain any propellant, such as is commonly present in a propellant-driven aerosol formulation.

In a preferred embodiment liquid and gel-spray formulations according to the invention may be adapted for application to the buccal mucosae.

As a result of direct investigation, it has been found that in some circumstances there may be limitations on the applicability of medicaments to the mucosal surface under the tongue, which limit the usefulness of sublingual applications. Certain highly lipid-soluble medicaments (including cannabinoids and extracts of cannabis) can only be brought into solution by dissolving in (principally) non-aqueous solvents. These solvents, such as propylene glycol, ethanol (with or without the addition of glycols) and solubilising agents, are pharmaceutically acceptable but when dropped or sprayed onto the sublingual mucosae (and dependent on concentration of ethanol) may produce a hot stinging sensation. The stinging sensation so produced may cause reflex swallowing. The result is that a proportion of the dose may then be swallowed by stimulation of the swallowing reflex. A variable proportion of the dose is absorbed from the GIT below the level of the oropharynx and is subject to the variability of absorption due to the first pass effect. These factors lead to variable absorption of medicaments by what is assumed to be the sublingual route.

It has been found that application of solutions or emulsifiable formulations direct to the buccal surface, either as drops or preferably as a pump action spray, solves the first pass problem and has a number of other unexpected advantages, as follows:

(1) When a conventional pressurised aerosol is directed into the oropharyngeal space, a cloud of particles can be seen escaping from the mouth indicating loss of medicament. This can be avoided by spraying directly onto the buccal surface, away from the area under the tongue. The problem can be more completely addressed by using a pump action, manually-operated spray (PAS). The PAS operates at lower pressure, produces a spray with a larger mean aerodynamic diameter (e.g. between 15 and 45 microns) and can be directed to the buccal rather than sublingual areas of the mouth;

(2) Avoidance or minimisation of the unacceptable stinging sensation (the buccal mucosa is less sensitive than the sublingual area in this respect);

(3) Substantial immobilisation of the dose of medicament in contact with the buccal surface, allowing for absorption from a site not disturbed by normal salivation. After application, the buccal mucosa returns to its normal position in apposition to the outer gingival surface of the maxilla or mandible and is there held in a pocket in contact with absorbing surfaces;

(4) Minimisation of loss of dose by swallowing. The swallowing reflex is not stimulated by buccal application, and because the medicament is in a closed space it is possible for the patient to swallow saliva produced normally without disturbing the buccal pocket;

(5) The area under the absorption curve (AUC) is similar for sublingual and buccal formulations, for cannabinoids. After buccal administration there is a substantial reduction in the amount of the primary (11-hydroxy-) metabolite of the cannabinoids. This confirms that a greater proportion of cannabinoid/active is absorbed transmucosally than from the sublingual area. A higher degree of absorption is taking place from the buccal mucosae than from the sublingual mucosae following the use of the buccal formulations described below (see Example 12).

Nature of the Lipophilic Medicament

The examples illustrate the way in which sublingual and buccal formulations can be made from intractable, lipophilic drug substances such as cannabinoids or glyceride trinitrate (GTN). However, the utility of the invention is not limited to this class of active ingredient and Table 1 lists some of the active ingredients by reference to class, and individual drugs which can be formulated according to the present invention.

Where medicaments are soluble in water it is possible to disperse the medicament over the epithelium of the buccal cavity and the sublingual mucosae. Provided that the medicament molecule (if ionised) has the appropriate ionisation constant, it will pass through the epithelium and be absorbed into the systemic circulation. Uncharged, lipid molecules will only pass into, and through, the oropharyngeal mucosae if they are brought into intimate contact with the mucosae.

Where medicaments are water insoluble, dispersion of oily materials in the aqueous environment of the mouth is uneven. When oily medicaments are brought into intimate contact with the mucosae there is an opportunity for absorption through the epithelium. However, oily substances have an unpleasant mouth feel generally, and it is necessary to formulate them in order to overcome this problem. Emulsions have a mouthfeel which is more acceptable than oil to most patients. Compliance (i.e. temporary abstinence from swallowing) is therefore improved.

Cannabinoids, the active constituents of cannabis, are soluble in highly non-polar solvents (i.e. in substances such as chloroform, dichloromethane and high concentrations of alcohol); they also have limited solubility in glycols. Some of these solvents are pharmaceutically unacceptable, and the pharmaceutically acceptable solvents need to be used in high concentrations to produce solutions which can be applied to the oral mucosa. Solubility in some of these solvents imposes a ceiling on the dose which can be given using conventional pharmaceutical methods of formulation.

In order to be absorbed from the sublingual/buccal mucosae it is essential that the cannabinoid is brought into intimate contact with the surface of mucosal cells. To this extent the formulation must be "wettable". Tetrahydrocannabinol (THC) is an oily liquid at room temperature; cannabidiol is an oil soluble solid. Both have very low solubility in aqueous excipients.

By direct experiment it has been discovered that formulation of a cannabinoid with at least one self-emulsifying surfactant, surprisingly results in the generation of an oil in water (o/w) emulsion in a few seconds, i.e. as soon as the product is wetted by saliva. Viscolising agents, optionally with adhesive properties, may be added to the formulation to ensure that the emulsion so formed adheres to the epithelium of the buccal cavity. Carbohydrate-based viscolisers are degraded by amylolytic enzymes in saliva and a combination of viscolisers can be devised such that there is progressive reduction in viscosity with dwell time in the buccal cavity. Advantage can also be taken of the effect of certain glycols and sugar alcohols which enhance formulations containing cannabinoids by, for example, allowing ethanol levels to be reduced. Sugars, which are rapidly soluble, speed dissolution. Where it is necessary to use non-cariogenic solubilisers, sugar alcohols are used preferentially.

Therefore, in accordance with a third aspect of the invention there is provided pharmaceutical formulation for use in administration of a lipophilic medicament via a mucosal surface, which formulation comprises at least one lipophilic medicament and at least one self emulsifying agent, wherein upon hydration the formulation forms an emulsion containing the lipophilic medicament which is capable of adhering to a mucosal surface and allowing controlled release of the medicament, wherein the lipophilic medicament is at least one extract from a cannabis plant.

A "plant extract" is an extract from a plant material as defined in the Guidance for Industry Botanical Drug Products Draft Guidance, August 2000, U.S. Department of Health and Human Services, Food and Drug Administration Centre for Drug Evaluation and Research.

"Plant material" is defined as a plant or plant part (e.g. bark, wood, leaves, stems, roots, flowers, fruits, seeds, berries or parts thereof) as well as exudates.

The term "Cannabis plant(s)" encompasses wild type *Cannabis sativa* and also variants thereof, including cannabis chemovars which naturally contain different amounts of the individual cannabinoids, *Cannabis sativa* subspecies *indica* including the variants var. *indica* and var. *kafiristanica*, *Cannabis indica* and also plants which are the result of genetic crosses, self-crosses or hybrids thereof. The term "Cannabis plant material" is to be interpreted accordingly as encompassing plant material derived from one or more cannabis plants. For the avoidance of doubt it is hereby stated that "cannabis plant material" includes dried cannabis biomass.

In the context of this application the terms "cannabis extract" or "extract from a cannabis plant", which are used interchangeably encompass "Botanical Drug Substances" derived from cannabis plant material. A Botanical Drug Substance is defined in the Guidance for Industry Botanical Drug Products Draft Guidance, August 2000, U.S. Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of cannabis, "botanical drug substances" derived from cannabis plants do not include highly purified, Pharmacopoeial grade cannabinoids.

"Botanical drug substances" derived from cannabis plants include primary extracts prepared by such processes as, for example, maceration, percolation, extraction with solvents such as C1 to C5 alcohols (e.g. ethanol), Norflurane (HFA134a), HFA227 and liquid carbon dioxide under pressure. The primary extract may be further purified for example by supercritical or subcritical extraction, vaporisation and chromatography. When solvents such as those listed above are used, the resultant extract contains non-specific lipid-soluble material. This can be removed by a variety of processes including "winterisation", which involves chilling to −20° C. followed by filtration to remove waxy ballast, extraction with liquid carbon dioxide and by distillation.

Preferred "cannabis extracts" include those which are obtainable by using any of the methods or processes specifically disclosed herein for preparing extracts from cannabis plant material. The extracts are preferably substantially free of waxes and other non-specific lipid soluble material but preferably contain substantially all of the cannabinoids naturally present in the plant, most preferably in substantially the same ratios in which they occur in the intact cannabis plant.

Botanical drug substances are formulated into "Botanical Drug Products" which are defined in the Guidance for Industry Botanical Drug Products Draft Guidance, August 2000, U.S. Department of Health and Human Services, Food and Drug Administration Centre for Drug Evaluation and Research as: "A botanical product that is intended for use as a drug; a drug product that is prepared from a botanical drug substance."

In accordance with a fourth aspect of the invention there is provided a pharmaceutical formulation for use in administration of a lipophilic medicament via a mucosal surface, which formulation comprises at least one lipophilic medicament and at least one self emulsifying agent, wherein upon hydration the formulation forms an emulsion containing the lipophilic medicament which is capable of adhering to a mucosal surface and allowing controlled release of the medicament, wherein the lipophilic medicament comprises a combination of two or more natural or synthetic cannabinoid.

In this embodiment the "cannabinoids" may be highly purified, Pharmacopoeial Grade substances and may be obtained by purification from a natural source or via synthetic means. The cannabinoids will include, but are not limited to, tetrahydrocannabinoids, their precursors, alkyl (particularly propyl) analogues, cannabidiols, their precursors, alkyl (particularly propyl) analogues, and cannabinol.

In a preferred embodiment the lipophilic medicament comprises any combination of two or more cannabinoid selected from tetrahydrocannabinol, $\Delta^9$-etrahydrocannabinol, $\Delta^9$-tetrahydrocannabinol propyl analogue, cannabidiol, cannabidiol propyl analogue, cannabinol, cannabichromene, cannabichromene propyl analogue and cannabigerol.

The principles of formulation suitable for administration of cannabis extracts and cannabinoids can also be applied to other medicaments such as alkaloids, bases and acids. The requirements are that, if the medicament is insoluble in saliva, it should be solubilised and/or brought into the appropriate unionised form by addition of buffering salts and pH adjustment.

The formulations according to the invention may be used for delivery of extracts of the cannabis plant and also individual cannabinoids, or synthetic analogues thereof, whether or not derived from cannabis plants and combinations of cannabinoids. "Cannabis plants" includes wild type *Cannabis sativa* and variants thereof, including cannabis chemovars which naturally contain different amounts of the individual cannabinoids. In particular, the invention provides formulations of cannabis based medicine extracts (CBME).

Cannabis has been used medicinally for many years, and in Victorian times was a widely used component of prescription medicines. It was used as a hypnotic sedative for the treatment of "hysteria, delirium, epilepsy, nervous insomnia, migraine, pain and dysmenorrhoea". The use of cannabis continued until the middle of the twentieth century, and its usefulness as a prescription medicine is now being re-evaluated. The discovery of specific cannabinoid receptors and new methods of administration have made it possible to extend the use of cannabis-based medicines to historic and novel indications.

The recreational use of cannabis prompted legislation which resulted in the prohibition of its use. Historically, cannabis was regarded by many physicians as unique; having the ability to counteract pain resistant to opioid analgesics, in conditions such as spinal cord injury, and other forms of neuropathic pain including pain and spasm in multiple sclerosis.

In the United States and Caribbean, cannabis grown for recreational use has been selected so that it contains a high content of tetrahydrocannabinol (THC), at the expense of other cannabinoids. In the Merck Index (1996) other cannabinoids known to occur in cannabis such as cannabidiol and cannabinol were regarded as inactive substances. Although cannabidiol was formerly regarded as an inactive constituent there is emerging evidence that it has pharmacological activity, which is different from that of THC in several respects. The therapeutic effects of cannabis cannot be satisfactorily explained just in terms of one or the other "active" constituents.

It has been shown that tetrahydrocannabinol (THC) alone produces a lower degree of pain relief than the same quantity of THC given as an extract of cannabis. The pharmacological basis underlying this phenomenon has been investigated. In some cases, THC and cannabidiol (CBD) have pharmacological properties of opposite effect in the same preclinical tests, and the same effect in others. For example, in some clinical studies and from anecdotal reports there is a perception that CBD modifies the psychoactive effects of THC. This spectrum of activity of the two cannabinoids may help to explain some of the therapeutic benefits of cannabis grown in different regions of the world. It also points to useful effects arising from combinations of THC and CBD. These have been investigated by the applicant. Table 3 below shows the difference in pharmacological properties of the two cannabinoids.

TABLE 3

| Effect | THC | THCV | CBD | CBDV | Reference |
|---|---|---|---|---|---|
| $CB_1$ (Brain receptors) | ++ |  | ± |  | Pertwee et al, 1977 |
| $CB_2$ (Peripheral receptors) | + |  | − |  |  |

TABLE 3-continued

| | THC | THCV | CBD | CBDV | Reference |
|---|---|---|---|---|---|
| CNS Effects | | | | | |
| Anticonvulsant † | -- | | ++ | | Carlini et al, 1977 |
| Antimetrazol | - | | - | | GW Data |
| Anti-electroshock | - | | ++ | | GW data |
| Muscle Relaxant | -- | | ++ | | Petro, 1980 |
| Antinociceptive | ++ | | + | | GW data |
| Catalepsy | ++ | | ++ | | GW data |
| Psychoactive | ++ | | - | | GW data |
| Antipsychotic | - | | ++ | | Zuardi et al, 1998 |
| Neuroprotective antioxidant activity* | + | | ++ | | Hampson A J et al 1998 |
| Antiemetic | ++ | | - | | |
| Sedation (reduced spontaneous activity) | + | | + | | Zuardi et al, 1998 |
| Appetite stimulation | ++ | | | | |
| Appetite suppression | - | ++ | | | |
| Anxiolytic | | | | | GW data |
| Cardiovascular Effects | | | | | |
| Bradycardia | - | | + | | Smiley et al, 1977 |
| Tachycardia | + | | - | | |
| Hypertension § | + | | - | | |
| Hypotension § | - | | + | | Adams et al, 1977 |
| Anti-inflammatory Immunomodulatory/ anti-inflammatory activity | ± | | ± | | Brown, 1998 |
| Raw Paw Oedema Test | - | | ++ | | GW data |
| Cox 1 | | | | | GW data |
| Cox 2 | | | | | GW data |
| TNFa Antagonism | + | + | ++ | ++ | |
| Glaucoma | ++ | | + | | |

*Effect is CB1 receptor independent.
† THC is pro convulsant
§ THC has a biphasic effect on blood pressure; in naive patients it may produce postural hypotension and it has also been reported to produce hypertension on prolonged usage.
GW Internal Report No 002/000159.

From these pharmacological characteristics and from direct experiments carried out by the applicant it has been shown, surprisingly, that combinations of THC and CBD in varying proportions are particularly useful in the treatment of certain therapeutic conditions. It has further been found clinically that the toxicity of a mixture of THC and CBD is less than that of THC alone.

Accordingly, in a fifth aspect the present invention provides pharmaceutical formulations comprising cannabinoids which have specific ratios of CBD to THC, which have been found to be clinically useful in the treatment or management of specific diseases or medical conditions.

In a further aspect the invention also provides pharmaceutical formulations which have specific ratios of tetrahydrocannabinovarin (THCV) or cannabidivarin (CBDV). THCV and CBDV (propyl analogues of THC and CBD, respectively) are known cannabinoids which are predominantly expressed in particular Cannabis plant varieties and it has been found that THCV has qualitative advantageous properties compared with THC and CBD respectively. Subjects taking THCV report that the mood enhancement produced by THCV is less disturbing than that produced by THC. It also produces a less severe hangover.

In a still further aspect the invention provides pharmaceutical formulations which have specific ratios of THCV to THC. Such formulations have been found to be particularly useful in the field of pain relief and appetite stimulation.

In a preferred embodiment the formulations provided in accordance with the fifth and subsequent aspects of the invention, e.g. formulations containing specific ratios of cannabinoids may also have all the essential features of the "self-emulsifying" formulations described above.

The invention also provides methods of making the aforementioned pharmaceutical formulations as well as methods of using them to treat or manage specific diseases or conditions. Embodiments of formulations, methods and uses of the present invention are set out in the accompanying claims.

It has particularly been observed by the present applicants that the combinations of the specific cannabinoids are more beneficial than any one of the individual cannabinoids alone. Preferred embodiments are those formulations in which the amount of CBD is in a greater amount by weight than the amount of THC. Such formulations are designated as "reverse-ratio" formulations and are novel and unusual since, in the various varieties of medicinal and recreational Cannabis plant available world-wide, CBD is the minor cannabinoid component compared to THC. In other embodiments THC and CBD or THCV and CBDV are present in approximately equal amounts or THC or THCV are the major component and may be up to 95.5% of the total cannabinoids present.

Particularly preferred embodiments and the target medical conditions for which they are suitable are shown in Table 4 below.

TABLE 4

Target Therapeutic Groups for Different Ratios of Cannabinoid

| Product group | Ratio THC:CBD | Target Therapeutic Area |
|---|---|---|
| High THC | >95:5 | Cancer pain, migraine, appetite stimulation |
| Even ratio | 50:50 | Multiple sclerosis, spinal cord injury, peripheral neurogenic neuropathy, other neurogenic pain. |
| Reverse/ Broad ratio CBD | <25:75 | Rheumatoid arthritis, Inflammatory bowel diseases. |
| High CBD | <5:95 | Psychotic disorders (schizophrenia), Epilepsy & movement disorders Stroke, head injury, Disease modification in RA and other inflammatory conditions Appetite suppression |

The pharmaceutical formulations of the invention may be formulated from pure cannabinoids in combination with pharmaceutical carriers and excipients which are well-known to those skilled in the art. For example CBD and THC can be purchased from Sigma-Aldrich Company Ltd, Fancy Road, Poole Dorset, BH12 4QH. CBDV and THCV may be extracted from Cannabis plants using techniques well-known to those skilled in the art. Working with Cannabis plants and cannabinoids may require a government licence in some territories but governments readily make such licences available to parties who apply for the purposes of medicinal research and commercial development of medicines. In the UK a licence may be obtained from the Home Office.

In preferred embodiments of the invention the formulations comprise extracts of one or more varieties of whole Cannabis plants, particularly *Cannabis sativa*, *Cannabis*

*indica* or plants which are the result of genetic crosses, self-crosses or hybrids thereof. The precise cannabinoid content of any particular cannabis variety may be qualitatively and quantitatively determined using methods well known to those skilled in the art, such as TLC or HPLC. Thus, one may chose a Cannabis variety from which to prepare an extract which will produce the desired ratio of CBD to THC or CBDV to THCV or THCV to THC. Alternatively, extracts from two of more different varieties may be mixed or blended to produce a material with the preferred cannabinoid ratio for formulating into a pharmaceutical formulation.

The preparation of convenient ratios of THC- and CBD-containing medicines is made possible by the cultivation of specific chemovars of cannabis. These chemovars (plants distinguished by the cannabinoids produced, rather than the morphological characteristics of the plant) can be been bred by a variety of plant breeding techniques which will be familiar to a person skilled in the art. Propagation of the plants by cuttings for production material ensures that the genotype is fixed and that each crop of plants contains the cannabinoids in substantially the same ratio.

Furthermore, it has been found that by a process of horticultural selection, other chemovars expressing their cannabinoid content as predominantly tetrahydrocannabinovarin (THCV) or cannabidivarin (CBDV) can also be achieved.

Horticulturally, it is convenient to grow chemovars producing THC, THCV, CBD and CBDV as the predominant cannabinoid from cuttings. This ensures that the genotype in each crop is identical and the qualitative formulation (the proportion of each cannabinoid in the biomass) is the same. From these chemovars, extracts can be prepared by the similar method of extraction. Convenient methods of preparing primary extracts include maceration, percolation, extraction with solvents such as C1 to C5 alcohols (ethanol), Norflurane (HFA134a), HFA227 and liquid carbon dioxide under pressure. The primary extract may be further purified for example by supercritical or subcritical extraction, vaporisation and chromatography. When solvents such as those listed above are used, the resultant extract contains non-specific lipid-soluble material. This can be removed by a variety of processes including chilling to −20° C. followed by filtration to remove waxy ballast, extraction with liquid carbon dioxide and by distillation. Preferred plant cultivation and extract preparation methods are shown in the Examples. The resulting extract is suitable for incorporation into pharmaceutical preparations. Methods of administration may be based on sublingual drops, sublingual tablets, gels and sprays, aerosol inhalations, vaporisers, other conventional pharmaceutical oral dosage forms, enemas and rectal suppositories. Other possible formulations are recited in the accompanying claims. Most preferably, the extracts may be formulated into self-emulsifying formulations according to the first and second aspects of the present invention.

There are advantages and disadvantages attached to each of these routes of administration. In general, preparations administered via the respiratory tract, oral/nasal tract and the distal rectum avoid the hepatic first pass effect. Medicaments swallowed are subject to substantial metabolism during their first pass through the liver, and the pattern of metabolites produced may vary according to the route of administration.

There are a number of therapeutic conditions which may be treated effectively by cannabis. The proportion of different cannabinoids in such preparations determines the specific therapeutic conditions which are best treated, and the present invention addresses the formulations which are most suitable for this purpose. As aforesaid the teaching of the invention is illustrated by the use of preparations containing specific ratios of cannabinoid (Table 4), and is further illustrated by the examples.

By direct experiment, it has been shown that administration of CBD (or CBDV) before the administration of THC modifies the cognitive effects experienced. The psychoactive effects of THC are diminished, and subsequent sedation is postponed and mitigated. This reduction is not observed if the THC is given before CBD. Accordingly, one preferred embodiment of the invention is a tablet for buccal or sublingual administration that has a rapidly soluble layer of CBD or CBDV, and a second layer or core of less rapidly soluble THC or THCV. The formulation thus provides a means of making medicaments available for absorption in a timed sequence. Indeed a variety of formulations having modified release profiles which comprise at least two phases can be formulated.

It is a further observation of the present applicants that CBD is able to act as a pharmaceutical stabilizer of pharmaceutical formulations and thus prolong shelf-life. Without being bound by theory it is thought that this may be due to anti-oxidant properties of CBD. Although its anti-oxidant properties are known to be useful in a pharmacological setting in relation to living matter, its effects as a pharmaceutical stabilizer have not previously been observed.

Accordingly, in another of its aspects the invention relates to the use of CBD to extend the shelf-life of a pharmaceutical product which comprises one or more biologically active components. Preferred biologically active components are set forth in the accompanying claims and may be one or more of the classes of medicaments and specific medicaments shown in Table 1 above.

The invention will be further understood with reference to the following examples, together with the accompanying Figures in which:

FIG. 1 schematically illustrates the packaging of one example of a dosage form according to the invention. (a) cross section at A-A, (b) sealed product in foil packaging, (c) perforation, (d) opened pack, (e) product ready for use.

FIG. 2 schematically illustrates the application of a dosage form according to the invention to the maxillary fossa.

FIG. 3 schematically illustrates the dosage form in place.

FIG. 4 schematically illustrates typical staining of the mucosa which would be observed after the dosage form has been in place for a period of 1 minute.

FIG. 8 is a flow chart showing the process of manufacture of extract from the High-THC and High-CBD chemovars.

EXAMPLE 1

Figure 1:
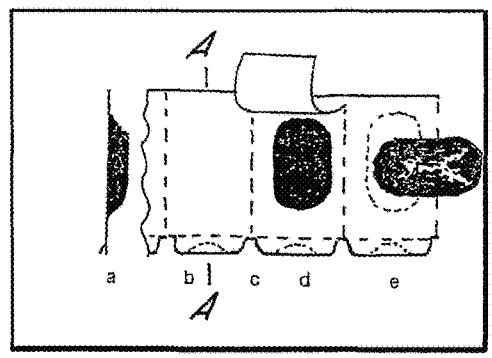
Figure 2:
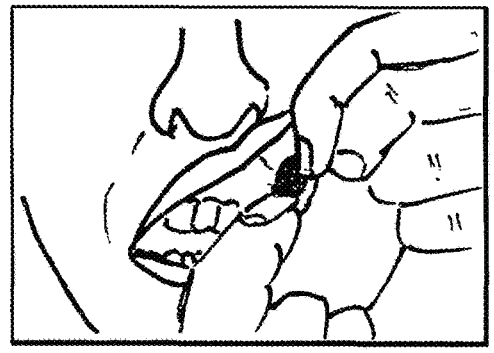

A 10% solution of pre-gelatinised starch (Component A) is made by dispersing one part of powdered pre-gelatinised starch in 9 parts of water, heating until gelatinised and then cooling. Pre-gelatinised cornstarch is the subject of a monograph in the US National Formulary. This product is used as a component of other formulations given in later examples, and is referred to as "starch gel". It has a negative surface charge.

EXAMPLE 2

There follows a description of the preparation of a formulation according to the invention in which hop extract, which is an oily resinous material, is used as a surrogate active ingredient. It has a bitter taste and this allows the patient to discern immediately when the active ingredient has stimulated the taste buds, and by implication has interacted with the mucosae. The dispersion of the formulation over the buccal and sublingual mucosae is revealed by the spread of colour. Any increased desire on the part of the patient to swallow the formulation can also be measured by direct observation.

In this example, a formulation is made by bringing together a gel (containing at least one active component which has a negative surface charge) together with a gel of opposing surface charge. The gel of opposing surface charge may contain optionally at least one active component which may be the same as that in the gel of opposite charge or another active ingredient. When the gels of opposing surface charge are brought together coacervation occurs resulting in a change in viscosity although the resulting gel is still thermoplastic and capable of being dispensed into moulds. On cooling the gel sets into a flexible but rigid gel.

Glycogelatin is prepared by heating bovine or porcine gelatine, or fish gelatine (isinglass) 18 parts and glycerol 2 parts on a water bath with distilled water sufficient to produce a final weight of 100 parts by weight. The glycogelatin so produced is a clear, rigid gel which surprisingly is inherently stable. It is resistant to microbial attack and is in equilibrium with air at a relative humidity of 60-70%.

A formulation is prepared from:

| | |
|---|---|
| Glyceryl monostearate (SE) | 5 parts |
| Soy lecithin | 7 parts |
| Chlorophyll (oil-soluble) | 3 parts |
| Component A | 30 parts |
| a-Tocopherol BP | 0.1 part |
| Extract of hops | 10 parts |
| Glycogelatin to produce | 100 parts |

The mixture is heated, with stirring to a temperature of 90° C. (using a water bath or in a microwave oven). The mixture is thoroughly stirred and while still molten 2 g aliquots are dispensed into aluminium foil moulds which have been treated with a releasing agent. A range of releasing agents is suitable for this purpose; a solution of silicone or beeswax in normal hexane is sprayed onto the concave mould, and the solvent allowed to evaporate. The weight of finished product can be varied to accommodate quantities of cannabis extract up to approximately 250 mg per piece representing a content of approximately 150 mg of THC or CBD.

When cool, a foil laminate is placed over the mould and sealed by the application of heat. Evacuation of air and replacement with nitrogen is carried out before final sealing so that the small, residual space in the finished dose unit is an inert, non-oxidising atmosphere.

The product so formed is a lenticular ovate gel which has one convex surface and one plain surface. It contains a colouring agent which is oil soluble and indicates the pattern of distribution of emulsion over the buccal cavity. Incorporation of chlorophyll as a disclosing agent is an optional feature; where used it indicates the areas of buccal mucosae to which a product containing medicament would also spread. These features of the invention are illustrated in FIGS. 1-4. It will be clear to a person skilled in the art that variations in the emulsifiers and the physical shape and form of packaging are within the teaching of the invention.

EXAMPLE 3

The formulation described above produces a product which is an elastic but rigid gel. When half of the tablet is placed between the upper jaw and the inside of the mouth (maxillary fossa) on either side, it starts to melt within one minute and at two minutes has produced an emulsified mass which covers the buccal mucosae. The gel does not produce a discernible sensation when placed between the maxilla and buccal mucosae, and does not induce a desire on the part of the subject to swallow the preparation. The area of buccal mucosae which is covered can be demonstrated by a photographic record taken before, one minute, two minutes, five minutes and 10 minutes, or other convenient time interval after the dosing.

This formulation has a slight taste characteristic of chlorophyll and extract of hops which was discernible for up to 10 minutes after placing the gel in situ, and thus demonstrates the presence of "released medicament" in the oropharynx over this period of time.

Figure 3:
Figure 4:
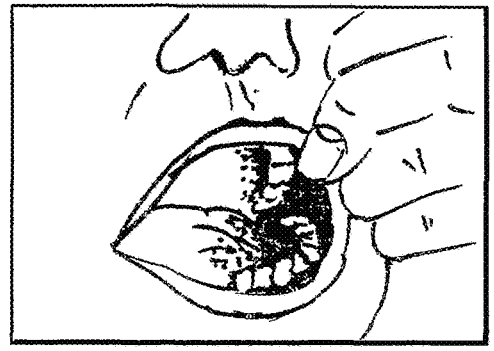
Figure 5:
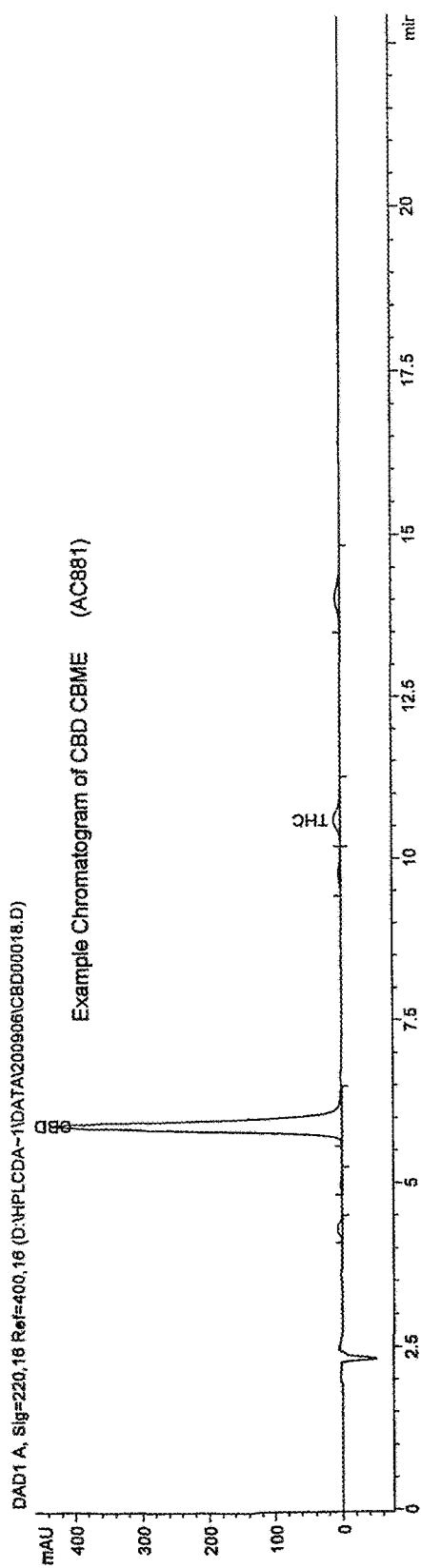
FIG. 5 is a sample HPLC chromatogram for CBD herbal drug extract.
Figure 6:
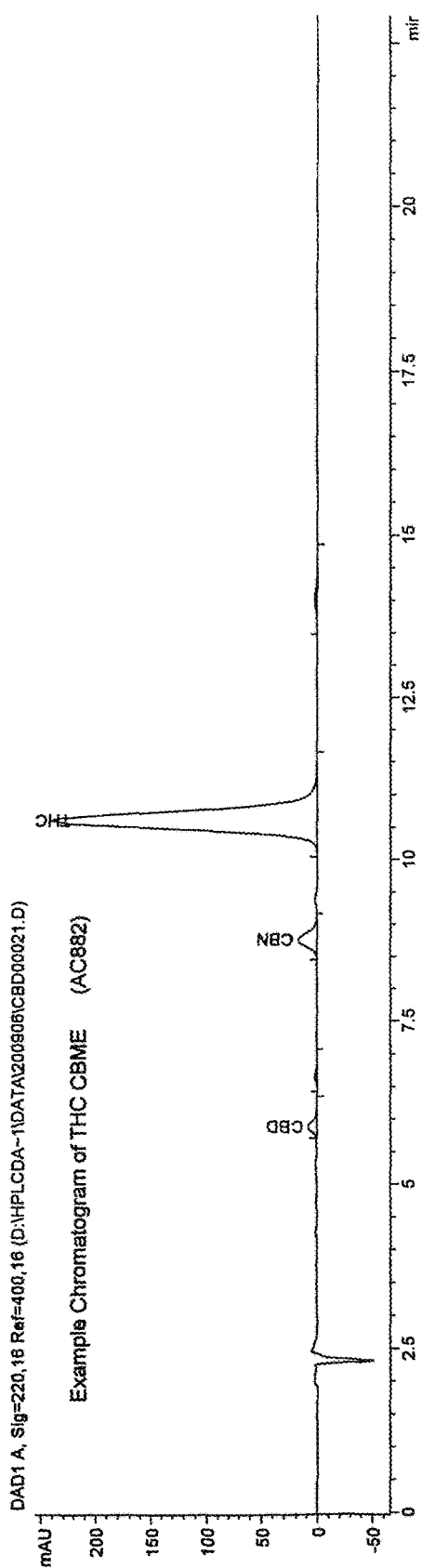
FIG. 6 is a sample HPLC chromatogram for THC herbal drug extract.

The distribution of colour (within one minute, and the persistence of taste for up to 10 minutes) indicates that this type of formulation is suitable as a vehicle for administration of highly lipid soluble medicaments such as cannabis extract or cannabinoids. As formulated, it can be used as a self-indicating placebo preparation in clinical trials. The accompanying Figures illustrate the distribution of one half of a product placed in the mouth. The configuration of the product, and the area of distribution of the product when emulsified in situ is shown in FIGS. 1-4. FIG. 3 shows the position in which the device is originally placed. For clarity of demonstration, the illustration shows the product placed on one side of the mouth. However, it may be divided and placed bilaterally to ensure maximal distribution. Alternatively, products containing different active ingredients can be placed simultaneously, but on separate sides of the mouth.

EXAMPLE 4

The device described in Example 1 is clamped between two pieces of nylon mesh and attached to the basket of tablet disintegration equipment (BP design) at a temperature of 35° C. The gel dispersed within 1-2 minutes to produce a fine even-textured emulsion.

EXAMPLE 5

This Example relates to the preparation of a dosage form containing a mixture of extracts of cannabis. The extracts of cannabis are referred to as Cannabis Based Medicine Extract (CBME) for ease of reference. An extract from a chemovar of cannabis producing more than 90% of its total cannabinoid as cannabidiol (CBD) may be prepared by supercritical fluid extraction of dried cannabis herb. This is referred to as CBME-G5. Similarly, an extract with a high proportion (more than 95%) total cannabinoid as tetrahydrocannabinol (THC) is referred to as CBME-G1. The formula in this example can be varied to accommodate CBME with greater or lesser content of cannabinoids, in order to achieve the desired ratio of THC to CBD, and other cannabinoids. Products containing different ratios of THC to CBD are useful for treatment of specific therapeutic conditions.

A mixture is produced by melting together the following ingredients:

| | |
|---|---|
| Glyceryl mono-oleate | 10 parts |
| Soy lecithin | 10 parts |
| Curcumin | 0.1 part |
| Component A | 20 parts |
| CBME —G5 to give CBD | 1 part |

| | | |
|---|---|---|
| CBME —G1 to give THC | 2 parts | |
| α-Tocopherol | 0.1 part | |
| Ascorbyl palmitate BP | 0.1 part | |
| Glycogelatin to produce | 100 parts | |

The components are mixed with gentle heat on a water bath, stirred and poured while hot into moulds. The product in moulds is finished as described in Example 1 and sealed under an atmosphere of inert gas.

In this formulation the curcumin imparts a bright yellow colour which allows the area of distribution of the product in the mouth to be identified. α-Tocopherol and ascorbyl palmitate are antioxidants which together with glyceryl mono oleate provide an effective antioxidant system.

The relatively large size (1-2 g) of this dosage form allows a comparatively large amount of active ingredient to be incorporated in the dosage form. Cannabidiol may be given in doses of 900 mg/day and the dosage form described allows this dose to be given in 2-9 (and preferably 2-4) divided doses per day.

Tetrahydrocannabinol is more active w/w than cannabidiol, and where a smaller unit dose of THC may be required it is possible to include this dose in a sublingual tablet of conventional size. Example 6 illustrates the formulation of such a tablet.

EXAMPLE 6

| | |
|---|---|
| Glyceryl monostearate (self emulsifying grade) | 5 parts |
| Polysorbate 80 | 0.5 parts |
| Lactose (direct compression grade) | 79.3 parts |
| Soluble starch | 10 parts |
| Tetrahydrocannabinol | 5 parts |
| Ascorbyl Palmitate | 0.1 part |
| α-Tocopherol | 0.1 part |
| Ethanol (dehydrated) BP | 10 parts |

The GMS, polysorbate, ascorbylpalmitate, a-Tocopherol and THC are dispersed and dissolved in the alcohol. The alcoholic solution is sprayed onto the dry powder ingredients which have been thoroughly mixed. Ethanol is allowed to evaporate and the granules are dusted with 1% of talc and compressed to a target tablet weight of 101 mg in a conventional tablet press. Biconvex punches with a diameter of 7 mm or 9 mm produce tablets with a high surface/weight ratio. These absorb water when placed in contact with the sublingual or buccal mucosae. The rate of dissolution can be adjusted by altering the degree of compression. Tablets compressed to a pressure of 1-3 Newtons give tablets which disperse in a period of 0.5 -5 minutes. The disintegration is determined by the method described in Example 4, and for these tablets was less than four minutes.

EXAMPLE 7

The generation of an emulsion from a self-emulsifying formulation is not limited to solid dosage forms. In the following example three liquid formulations suitable for sublingual application are exemplified. A solution is produced by melting together (at a temperature not exceeding 50° C.) the following ingredients (amounts given in parts by weight):—

| | A | B | C |
|---|---|---|---|
| Glyceryl mono-oleate (self-emulsifying) | 2 | 2 | 2 |
| Medium chain triglycerides | 5 | — | — |
| Cremophor RH40 | 30 | 26.5 | — |
| CBME | 10 | 10 | — |
| CBME-G1 to give THC | — | — | 5 |
| CBME-G5 to give CBD | — | — | 5 |
| α-Tocopherol | 0.1 | — | — |
| Ascorbyl palmitate | 0.1 | — | — |
| Propylene glycol | — | — | 44 |
| Ethanol BP | 52.8 | 61.5 | 44 |
| TOTAL | 100 | 100 | 100 |

The products formed by mixing these ingredients are dispensed in 10 ml quantities into a glass vial and closed with a pump action spray break-up button. Each 1 ml of product contains 100 mg of THC and each actuation of the pump delivers a fine spray which can be directed to the area of mucosae under the tongue.

Solutions of CBME in ethanol alone are not generally suitable to be used as a spray. The aggressive nature of pure ethanol as a solvent further limits the amount which can be applied to the mucosae without producing discomfort to the patient. Surprisingly, the addition of a self-emulsifying primary surfactant and solubiliser allows a greater quantity of cannabinoid to be contained in a unit dose. Spraying small quantities onto the sublingual or buccal mucosae results in evaporation of a significant amount of ethanol, and the emulsion so produced is non-irritant and does not stimulate the swallowing reflex. This provides greater dwell time for the in situ-formed emulsion to be in contact with the sublingual or buccal mucosae. A particular feature of this formulation is the accessory solvent activity of the medium chain triglycerides which also act as a secondary emulsifier.

Formulation "B" as listed above has a viscosity within the range of 100-350 centipoises.

EXAMPLE 8

The solid dosage form may be a soft gelatin capsule, which can be crushed to release the medicament to give an emulsion. The capsule can then be swallowed to provide the residue of the dose for absorption in the remainder of the gastrointestinal tract. The soft gelatin capsule provides an emulsified form of medicament which can be absorbed from any part of the GI tract. A capsule mass may be made from the following ingredients:—

| | |
|---|---|
| Glyceryl monostearate (self emulsifying) | 5 parts |
| Polysorbate 80 | 1 part |
| Beeswax | 5 parts |
| CBME G1 to give THC | 10 parts |
| CBME G5 to give CBD | 10 parts |
| α-tocopherol | 0.1 part |
| Ascorbyl palmitate | 0.1 part |
| Hemp oil to produce | 100 parts by weight |

EXAMPLE 9

A dosage form for buccal use which uses vegetable rather than animal gelling agents may be made as follows:

| | |
|---|---|
| Sorbitol | 35 parts |
| Gum Acacia | 20 parts |

| Glyceryl mono-oleate | 10 parts |
|---|---|
| Egg lecithin | 10 parts |
| CBME-1 to produce 5 mg THC | 5 parts |
| CBME-5 to produce 5 mg CBD | 5 parts |
| Tocopherol | 0.1 parts |
| Ascorbyl palmitate | 0.1 parts |
| Vanillin | 0.1 parts |
| BHT | 0.01 parts |
| Glycerol | 5.0 parts |
| Water | qs |

The fat soluble ingredients are melted together at a temperature of 70° C. Sorbitol is mixed with the Acacia gum, dispersed in glycerol, and added to the other solid ingredients. Water is added, and the mass heated on a boiling water bath until evenly dispersed/dissolved. While still at a temperature of 60° C. the mass is distributed into moulds (as described in Example 1). The mass can also be cast or rolled into a sheet, preferably 2.5 mm thick. Oval or hexagon-shaped pieces with an area of 40 mm² are cut and the pieces applied to a non-stick backing sheet larger than the piece, and covered with a non adhesive protective membrane. The patch so formed is sealed under an inert gas blanket into a pocket formed from heat-sealable foil laminate. The product so produced is suitable for treatment of patients suffering from migraine, arthritis, epilepsy, multiple sclerosis and other types of neuropathic and neurogenic pain, where it is necessary to have release of the medicament over a period of hours. Disintegration time for this formulation is greater than 90 minutes.

EXAMPLE 10

A product providing fast release of a constituent and a further release of constituent over a prolonged time can be produced by making a combination dose unit. Using the formulation described in Example 8, a quantity of heated mass is filled into a mould or cast into a film, and allowed to set. A layer of material as described in Example 5 is then cast onto the surface of the gel described in Example 9. The composite gel is then packaged as described in these examples. Variation of the proportions of mass in the two layers provides for modification of the kinetic profile produced by the dose unit.

In some circumstances it may be desirable to administer two drugs in a time dependent order. This can arise where one drug of the pair has a protective effect on the other. Example 10 describes a composite gel formulation of the type described in earlier examples. The formulation described in Example 11 provides CBD which is an antioxidant known to have a protective effect on THC to be made available for absorption through the buccal/sublingual mucosae just before THC. Cannabidiol is contained in the fast release layer and THC is dissolved out of the delayed release layer. Example 11 describes a dose unit consisting of two layers with differing dissolution characteristics.

EXAMPLE 11

| (a) Glyceryl mono-oleate | 7 parts |
|---|---|
| Soy lecithin | 7 parts |
| Acacia gum | 15 parts |
| Tetrahydrocannabinol | 10 parts |
| α-tocopherol | 0.1 parts |
| Xylitol | 5.1 parts |
| Glycerol | 3 parts |
| Purified Water | to produce 100 parts |

A molten mass is prepared as described in previous examples and aliquots cast into moulds or as a sheet.

| (b) Glyceryl mono-oleate | 15 parts |
|---|---|
| Soy lecithin | 10 parts |
| Component A | 20 parts |
| α-tocopherol | 0.1 parts |
| Cannabidiol | 20 parts |
| Glycogelatin to produce | 100 parts |

A mass is prepared as described in Example 2. The mass is cast as a second layer into a mould containing an aliquot of formulation (a). At the interface there is slight melting and bonding of the two components to give a coherent product. If the gel is cast into a concave mould, the product has a planar surface which, if placed in contact with the mucosa is the first to disperse and thus produces the required sequence of presentation of components for absorption.

A layer of formulation (b) can be cast on the surface of a sheet of formulation (a). The two formulations contain colloidal components with opposing signs and at the zone of fusion good adhesion is produced by coacervation. The composite layer is then cut into shapes suitable for application to the oral mucosae. The product is packed as described in Example 3 and protected from air and light.

EXAMPLE 12

The following examples illustrate the distinctive features of formulations intended for spray application to the buccal mucosae, the method of application, and the blood levels produced by buccal absorption in comparison with sublingual administration.

The following are examples of a liquid formulations suitable for buccal administration. A solution is produced by dissolving (at a temperature not exceeding 50° C.) the following ingredients (quantitative details are expressed as parts by weight):—

|  | a | b | c | d | e |
|---|---|---|---|---|---|
| Glyceryl monostearate (self-emulsifying) | 2 | — | 2 | — | 2 |
| Glyceryl monooleate (self-emulsifying) | — | 2 | — | 2 | — |
| Cremophor RH40 | 20 | 30 | 30 | 20 | 30 |
| CBME-G1 to give THC | 5 | 10 | — | — | — |
| CBME-G5 to give CBD | — | — | 5 | 10 | — |
| CBME-G1 and G5 to give THC & CBD | — | — | — | — | 10 each |
| α-Tocopherol | 0.1 | 0.1 | 0.1 | 0.1 | 0.1 |
| Ascorbyl palmitate | 0.1 | 0.1 | 0.1 | 0.1 | 0.1 |
| Ethanol BP to produce | 100 | 100 | 100 | 100 | 100 |

Cannabis Based Medicine Extract (CBME) is an extract of cannabis which may be prepared by, for example, percolation with liquid carbon dioxide, with the removal of ballast by cooling a concentrated ethanolic solution to a temperature of −20° C. and removing precipitated inert plant constituents by filtration or centrifugation.

The product formed by mixing these ingredients is dispensed in 6 ml quantities into a glass vial and closed with a pump action spray. In use, the dose is discharged through a break-up button or conventional design. Proprietary devices that are suitable for this purpose are Type VP7 produced by Valois, but similar designs are available from other manufacturers. The vial may be enclosed in secondary packaging to allow the spray to be directed to a particular area of buccal mucosa. Alternatively, a proprietary button with an extension may be used to direct the spray to a preferred area of buccal mucosa.

Each 1 ml of product contains 50-100 mg of $\Delta^9$-tetrahydrocannabinol (THC) and/or cannabidiol (CBD). Each actuation of the pump delivers a spray which can be directed to the buccal mucosae. In the above formulations CBMEs of known cannabinoid strength are used. CBME-G1 is an extract from a high THC-yielding strain of cannabis, and CBME-G5 is from a high CBD-yielding variety. It will be clear to a person skilled in the art that purified cannabinoids, and extracts containing the cannabinoids, can be made formulated as described above by quantitative adjustment.

Although solutions of CBME in ethanol alone can be used as a spray, the quantity of cannabinoid that can be delivered is limited by the aggressive nature of pure ethanol in high concentration as a solvent. This limits the amount that can be applied to the mucosae without producing discomfort to the patient. When a group of patients received THC or CBD in a solution of the type described above, directing the spray either sublingually or against the buccal mucosa, the patients uniformly reported a stinging sensation with the sublingual application, but mild or no discomfort when the same solution was sprayed onto the buccal mucosa. It was further, surprisingly, found that the addition of a self-emulsifying primary surfactant as solubiliser allowed a greater quantity of cannabinoid to be contained in a unit dose. Spraying small quantities of this type of formulation onto the buccal mucosa does not appreciably stimulate the swallowing reflex. This provides greater dwell time for emulsion formed in situ to be in contact with the buccal surface.

Formulations were administered to a group of 13 human subjects so that they received 4 mg THC, 4 mg of CBD or placebo (vehicle alone) via a sublingual tablet, sublingual pump-action spray or buccal route.

Absorption [area under the absorption curve (AUC)] of cannabinoid and primary metabolite were determined in samples of blood taken after dosing. The following Table 5 gives these as normalised mean values.

TABLE 5

| Analyte in Plasma | Route of Administration | | |
|---|---|---|---|
| | PAS sublingual AUC | Sublingual tablet AUC | Oropharyngeal AUC |
| THC | 2158.1 | 1648.4 | 1575.0 |
| 11 OH THC | 3097.6 | 3560.5 | 2601.1 |
| CBD | 912.0 | 886.1 | 858.0 |

These results show that the total amounts of cannabinoid absorbed by sublingual and buccal (oropharyngeal) routes are similar but that there is a substantial (approximately 25%) reduction in the amount of 11 OH metabolite detected after oropharyngeal (buccal) administration. This finding is not inconsistent with reduced swallowing (and subsequent reduced hepatic) metabolism of the buccal formulation.

It is known that 11-hydroxy metabolite of THC is possibly more psychoactive than the parent compound. It is therefore desirable to minimise the amount of this metabolite during administration, and this is likely to be achieved by using a formulation and method of application which reduces the amount of a buccal or sublingual dose that is swallowed. The pump action spray appears to offer a simple means of reducing the amount of material that is swallowed and metabolised by absorption from the intestinal tract below the level of the oropharynx.

EXAMPLE 13

The use of a pump action dispenser makes it possible to dispense defined quantities of a gel with the required precision and repeatability for pharmaceutical applications. A gel is prepared from the following ingredients (parts by weight):—

| Carboxymethylcellulose Sodium | 2 |
|---|---|
| Glyceryl monostearate | 10 |
| Glycerol | 10 |
| CBME-G1 and G5 to give THC and CBD | 5 |
| Ethanol | 40 |
| Ascorbic Acid | 0.1 |
| Tocopherol | 0.1 |
| Water to | 100 |

The non-aqueous ingredients are melted together at a temperature of not more than 50° C. until evenly suspended. Water is then added to produce a viscous creamy gel, taking care not to introduce air during mixing. The product is dispensed into containers whilst still warm and sealed with a pump dispenser head (type 251/331) supplied by Valois. The head on this device delivers a ribbon of gel, and when pressure is removed, there is sufficient retraction of gel to ensure that particles of gel are not left exposed. The quantity of gel can be directed to accessible buccal surfaces, where it adheres. When the buccal surface returns to its normal position the mass of gel then absorbs more water from the available saliva and yields its charge of medicament.

EXAMPLE 14

Experiments have shown the effect of varying the amount of self-emulsifier and proportions of negative and positively charged viscolising agents on dissolution/disintegration time in the mouth.

Solid gel formulations as described in Examples 1 and 2 were prepared by dissolving the ingredients by heating in a microwave oven, until a uniform molten mass was produced. The molten mass was dispensed using a Gilson-type pipette directly into recycled blisters, which had been washed with 70% alcohol and air dried. Disintegration time was measured in a BP type apparatus.

The effects are described below:—

Disintegration time increases with increased mass:—

| | G001/A (i) | G001/A(ii) | G001(iii) |
|---|---|---|---|
| Mass (mg) | 586 | 807 | 2140 |
| $T_{dis}$ (m, s) | 920 | 1230 | 2110 |

Increasing emulsifier content increases $T_{dis}$:—

|  | G001A | G001B |
|---|---|---|
| % emuls | 10 | 20 |
| $T_{dis}$ | 1345 | 8730 |

Increasing gelatin content of gel has little effect on $T_{dis}$:—

|  | G001/A | G001/B |
|---|---|---|
| Mass (mg) | 1145 | 807 |
| % gelatin | 14 | 25 |
| $T_{dis}$ | 1345 | 1230 |

Addition of pre-gelatinised maize starch (PGMS) decreases $T_{dis}$:—

|  | G002/A(ii) | G003 |
|---|---|---|
| Mass (mg) | 807 | 751 |
| % PGMS | 0 | 2 |
| $T_{dis}$ | 920 | 405 |

EXAMPLE 15

Growing of Medicinal Cannabis

Plants are grown as clones from germinated seed, under glass at a temperature of 25° C.±1.5° C. for 3 weeks in 24 hour daylight; this keeps the plants in a vegetative state. Flowering is induced by exposure to 12 hour day length for 8-9 weeks.

No artificial pesticides, herbicides, insecticides or fumigants are used. Plants are grown organically, with biological control of insect pests.

Figure 7:
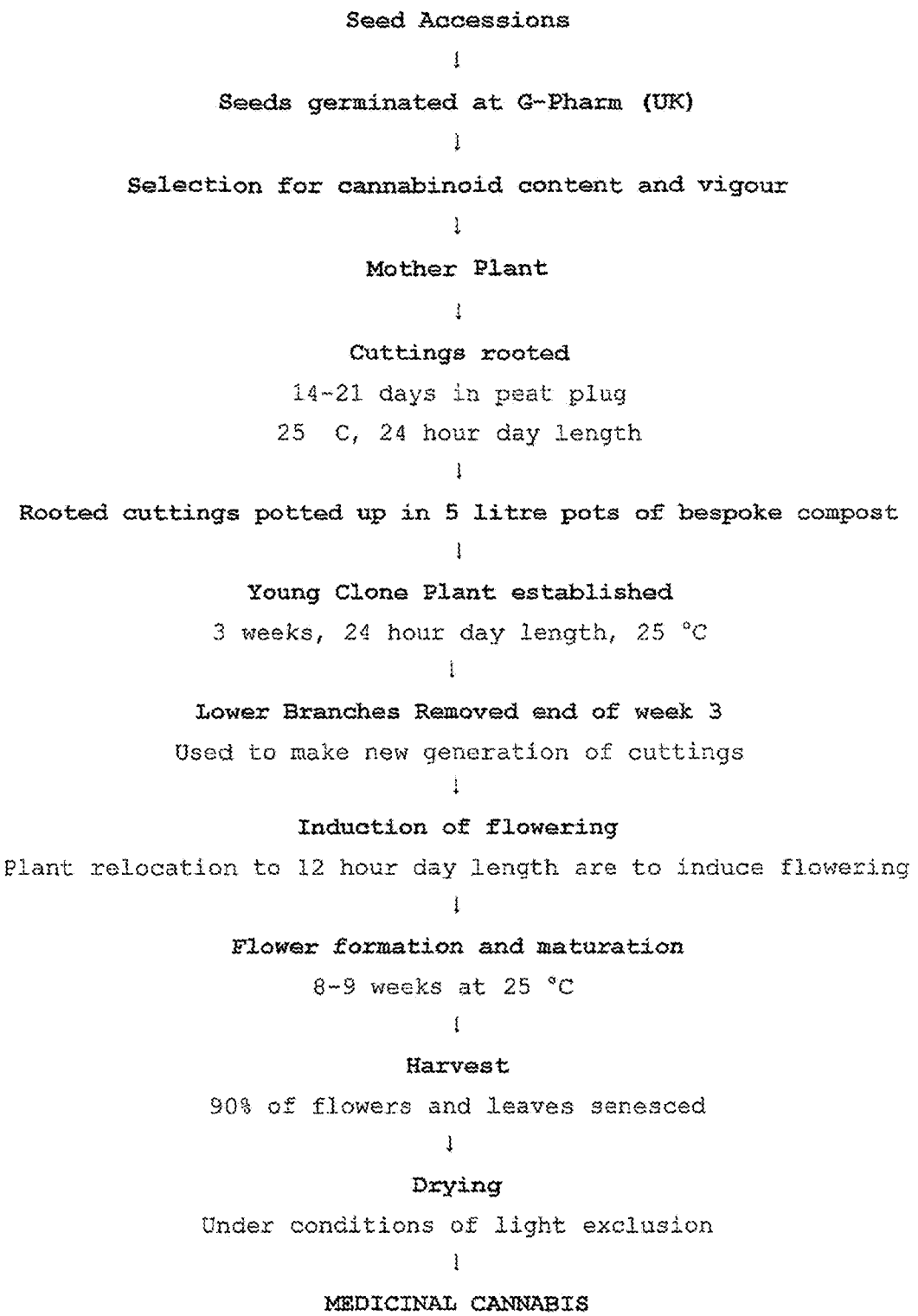
FIG. 7 is a summary of the essential steps in production from seed accession to dried Medicinal Cannabis.

The essential steps in production from seed accession to dried Medicinal Cannabis are summarised in FIG. 7.

EXAMPLE 16

Determination of Cannabinoid Content in Plants and Extracts

Identity by TLC
a) Materials and methods
Equipment Application Device Capable of Delivering an Accurately Controlled Volume of Solution i.e
  1 µl capillary pipette or micro liter syringe.
TLC development tank with lid
Hot air blower
Silica gel G TLC plates (SIL N-HR/UV254), 200 µm layer with fluorescent indicator on polyester support.
Dipping tank for visualisation reagent.

| Mobile phase | 80% petroleum ether 60:80/20% Diethyl ether. |
|---|---|
| Visualisation reagent | 0.1% w/v aqueous Fast Blue B (100 mg in 100 ml de-ionised water). An optional method is to scan at UV 254 and 365 nm. | b) Sample preparation
  i) Herbal Raw Material
    Approximately 200 mg of finely ground, dried cannabis is weighed into a 10 ml volumetric flask. Make up to volume using methanol:chloroform (9:1) extraction solvent.
    Extract by ultrasound for 15 minutes. Decant supernatant and use directly for chromatography.
  ii) Herbal Drug Extract
    Approximately 50 mg of extract is weighed into a 25 ml volumetric flask. Make up to volume using methanol solvent. Shake vigorously to dissolve and then use directly for chromatography.
c) Standards
  0.1 mg/ml delta-9-THC in methanol.
  0.1 mg/ml CBD in methanol.
  The standard solutions are stored frozen at −20° C. between uses and are used for up to 12 months after initial preparation.
d) Test solutions and method
  Apply to points separated by a minimum of 10 mm.
    i) either 5 µl of herb extract or 1 µl of herbal extract solution as appropriate,
    ii) 10 µl of 0.1 mg/ml delta-9-THC in methanol standard solution,
    iii) 10 µl of 0.1 mg/ml CBD in methanol standard solution.
  Elute the TLC plate through a distance of 8 cm, then remove the plate. Allow solvent to evaporate from the plate and then repeat the elution for a second time (double development).
  The plate is briefly immersed in the Fast Blue B reagent until the characteristic re/orange colour of cannabinoids begins to develop. The plate is removed and allowed to dry under ambient conditions in the dark.
  A permanent record of the result is made either by reproduction of the image by digital scanner(preferred option) or by noting spot positions and colours on a tracing paper.
Assay THC, THCA, CBD, CBDA and CBN by HPLC
a) Materials and methods

| Equipment: | HP 1100 HPLC with diode array detector and autosampler. The equipment is set up and operated in accordance with in-house standard operating procedures (SOPlab037) |
|---|---|
| HPLC column | Discovery C8 5 µm, 15 × 0.46 cm plus Kingsorb ODS2 precolumn 5 µm 3 × 0.46 cm. |
| Mobile Phase | Acetonitrile:methanol:0.25% aqueous acetic acid (16:7:6 by volume) |
| Column Operating Temperature | 25° C. |
| Flow Rate | 1.0 ml/min |
| Injection Volume | 10 µl |
| Run time | 25 mins |
| Detection | Neutral and acid cannabinoids 220 nm (band width 16 nm) Reference wavelength 400 nm/bandwidth 16 nm Slit 4 nm Acid cannabinoids are routinely monitored at 310 nm (band width 16 nm) for qualitative confirmatory and identification purposes only. |
| Data capture | HP Chemistation with Version A7.01 software | b) Sample preparation
  Approximately 40 mg of Cannabis Based Medicinal Extract is dissolved in 25 ml methanol and this solution is diluted to 1 to 10 in methanol. This dilution is used for chromatography.

0.5 ml of the fill solution, contained within the Pump Action Sublingual Spray unit, is sampled by glass pipette. The solution is diluted into a 25 ml flask and made to the mark with methanol. 200 µl of this solution is diluted with 800 µl of methanol.

Herb or resin samples are prepared by taking a 100 mg sample and treating this with 5 or 10 ml of Methanol/Chloroform (9/1 w/v). The dispersion is sonicated in a sealed tube for 10 minutes, allowed to cool and an aliquot is centrifuged and suitably diluted with methanol prior to chromatography.

c) Standards

External standardisation is used for this method. Dilution of stock standards of THC, CBD and CBN in methanol or ethanol are made to give final working standards of approximately accurately 0.1 mg/ml. The working standards are stored at −20° C. and are used for up to 12 months after initial preparation.

Injection of each standard is made in triplicate prior to the injection of any test solution. At suitable intervals during the processing of test solutions, repeat injections of standards are made. In the absence of reliable CBDA and THCA standards, these compounds are analysed using respectively the CBD and THC standard response factors. The elution order has been determined as CBD, CBDA, CBN, THC and THCA. Other cannabinoids are detected using this method and may be identified and determined as necessary.

d) Test solutions

Diluted test solutions are made up in methanol and should contain analytes in the linear working range of 0.02-0.2 mg/ml.

e) Chromatography Acceptance Criteria:

The following acceptance criteria are applied to the results of each sequence as they have been found to result in adequate resolution of all analytes (including the two most closely eluting analytes CBD and CBDA)

i) Retention time windows for each analyte:
CBD 5.4-5.9 minutes
CBN 7.9-8.7 minutes
THC 9.6-10.6 minutes ii) Peak shape (symmetry factor according to BP method)
CBD<1.30
CBN<1.25
THC<1.35 iii) A number of modifications to the standard method have been developed to deal with those samples which contain late eluting impurity peaks e.g method CBD2A extends the run time to 50 minutes. All solutions should be clarified by centrifugation before being transferred into autosampler vials sealed with teflon faced septum seal and cap.

iv) The precolumn is critical to the quality of the chromatography and should be changed when the back pressure rises above 71 bar and/or acceptance criteria regarding retention time and resolution, fall outside their specified limits.

f) Data Processing

Cannabinoids can be subdivided into neutral and acidic—the qualitative identification can be performed using the DAD dual wavelength mode. Acidic cannabinoids absorb strongly in the region of 220 nm-310 nm. Neutral cannabinoids only absorb strongly in the region of 220 nm. Routinely, only the data recorded at 220 nm is used for quantitative analysis.

The DAD can also be set up to take UV spectral scans of each peak, which can then be stored in a spectral library and used for identification purposes.

Data processing for quantitation utilises batch processing software on the Hewlett Packard Chemstation.

a) Sample Chromatograms

HPLC sample chromatograms for THC and CBD Herbal Drug extracts are provided in the accompanying Figures.

EXAMPLE 17

Preparation of the Herbal Drug Extract

A flow chart showing the process of manufacture of extract from the High-THC and High-CBD chemovars is shown in FIG. 8.

EXAMPLE 18

High THC cannabis was grown under glass at a mean temperature of 21+2° C., RH 50-60%. Herb was harvested and dried at ambient room temperature at a RH of 40-45% in the dark. When dry, the leaf and flower head were stripped from stem and this dried biomass is referred to as "medicinal cannabis".

Medicinal cannabis was reduced to a coarse powder (particles passing through a 3 mm mesh) and packed into the chamber of a Supercritical Fluid Extractor. Packing density was 0.3 and liquid carbon dioxide at a pressure of 600 bar was passed through the mass at a temperature of 35° C. Supercritical extraction is carried out for 4 hours and the extract was recovered by stepwise decompression into a collection vessel. The resulting green-brown oily resinous extract is further purified. When dissolved in ethanol BP (2 parts) and subjected to a temperature of −20° C. for 24 hours a deposit (consisting of fat-soluble, waxy material) was thrown out of solution and was removed by filtration. Solvent was removed at low pressure in a rotary evaporator. The resulting extract is a soft extract which contains approximately 60% THC and approximately 6% of other cannabinoids of which 1-2% is cannabidiol and the remainder is minor cannabinoids including cannabinol. Quantitative yield was 9% w/w based on weight of dry medicinal cannabis.

A high CBD chemovar was similarly treated and yielded an extract containing approximately 60% CBD with up to 4% tetrahydrocannabinol, within a total of other cannabinoids of 6% Extracts were made using THCV and CBDV chemovars using the general method described above.

A person skilled in the art will appreciate that other combinations of temperature and pressure (in the range +10° C. to 35° C. and 60-600 bar) can be used to prepare extracts under supercritical and subcritical conditions.

EXAMPLE 19

Street cannabis (marijuana) grown in the U.S. and Caribbean typically has a high percentage of total cannabinoid as THC; European (usually described as "Moroccan" cannabis) contains approximately equal quantities of THC and CBD. This may account for conflicting reports on the efficacy of cannabis in certain clinical studies. The applicant has sought to introduce precision in producing defined ratios of cannabinoid in two ways; by using mixtures of defined extracts and also by producing an extract from a single chemovar which produces the appropriate ratio of cannabinoids. Chemovars which express their cannabinoid content as predominantly one compound have been used to prepare the formulations of the invention but the teaching of the patent can be applied to synthetically produced cannabinoids or cannabinoids obtained by purification of cannabis Certain chemovars express an approximately 50:50 ratio of THCV/CBDV. It is therefore convenient to use a single plant extract to provide the ratio of cannabinoids. When the plants are grown from cuttings, the genotype is fixed and the ratio of cannabinoids is a constant. The overall yield may vary but this is factored into the quantity of extract used to provide a defined quantity of cannabinoid. A formulation which is particularly suitable for the treatment of multiple sclerosis is made to the following formula: CBME extract of chemovar G10 providing

|  | 5a | 5b | 5c |  |
|---|---|---|---|---|
| THCV | 0.1 | 2.5 | 10 | parts |
| CBDV | 0.1 | 2.5 | 10 | parts |
| Spray-dried lactose | 60 | 60 | 50 | parts |
| Dextrates | 37.7 | 21.5 | 16.5 | parts |
| Lecithin | 1 | 10 | 10 | parts |
| α-tocopherol | 0.1 | 2.5 | 2.5 | parts |
| Magnesium stearate | 1 | 1 | 1 | part |

The CBME-G1O extract is dissolved in 5 parts of ethanol and this solution used to mass the other ingredients. The mass is forced through a sieve, and the granules are dried at low temperature. When dry, the granules are dusted with magnesium stearate and compressed to 1.5 Newtons to give tablets suitable for sublingual administration to patients with multiple sclerosis, spinal chord injury, peripheral neuropathy or other neurogenic pain.

EXAMPLE 20

In order to make cannabidiol available before THC, a multi layered dosage form has been developed. In this exemplification, THC obtained either from synthetic or natural sources is contained in a core. CBD obtained from a natural source such as a cannabis chemovar extract or from synthetic material is present in the outer coating, which dissolves first and is followed by THC.

A two-layered tablet is formulated from the following ingredients.

| Inner Core: | |
|---|---|
| CBME-G1 providing THC | 2 parts |
| Direct compression lactose | 66.9 parts |
| Pre-gelatinised starch | 30 parts |
| α-tocopherol | 0.1 part |
| Magnesium stearate | 1 part |

The CBME is dissolved in sufficient ethanol for the whole to be sprayed onto the other dry ingredients. The powder is allowed to dry at room temperature and thoroughly mixed. Magnesium stearate is added and the tablets are compressed to a hardness of 6 Newtons. These cores can be pressed conveniently in a tablet press with 7 mm biconvex dies. When tested in a BP-type disintegration apparatus, disintegration time of these core tablets was 5-10 minutes.

Outer Layer:

The outer layer of tablets was prepared from the following ingredients:

| CBME-G5 | 8 parts |
|---|---|
| Glycerol monostearate | 5 parts |
| Lecithin | 5 parts |
| Direct compression lactose | 55 parts |
| Pre-gelatinised starch | 26.7 parts |
| α-tocopherol | 0.2 parts |
| Oil of Peppermint | 0.1 part |

Sufficient ethanol BP is used to dissolve the CBME extract which is then sprayed on to the other dry ingredients. Ethanol is allowed to evaporate at room temperature and the dry granules are thoroughly mixed and tableting arranged so that half of the charge is delivered into a 9 mm table die. The charge is lightly compressed (0.25 Newtons), a core as described above is added to each die, and the remainder of the tablet granules added to the die. Tablets are compressed to a hardness of 1.5 Newtons.

The tablets so produced have a soft outer coat which is compressed sufficiently hard to withstand limited handling, and are individually packed in blister packs to reduce friability. When the tablet is placed under the tongue, the soft outer core quickly disintegrates and forms a slightly gelatinous mass which yields CBD. The disintegration of this coating when tested in a BP model disintegration apparatus is 1-4 minutes. The harder core containing THC then dissolves and then yields THC for absorption after CBD has already been presented to the sublingual or buccal mucosae. By using a two-layered tablet in this way it is possible to optimise the sequence of presentation of cannabinoids. CBD absorbed first has an in vitro and in vivo antioxidant activity which is beneficial in enhancing the stability of THC and aiding its absorption. As the CBD component of the extract used to supply the THC component contains relatively small amounts of CBD which would act as antioxidant, additional tocopherol is included to act as a chemical antioxidant. The tablets so produced are useful in the treatment of multiple sclerosis and other neurogenic pains.

The same tablet mix when compressed to a hardness of 6 Newtons is also suitable for the treatment of rheumatoid arthritis and other inflammatory bowel diseases when given as an oral preparation intended to be swallowed.

Surprisingly, although it is reported that cannabis stimulates appetite, it has been shown by direct experiment that high CBD extracts decrease the food intake and weight gain of mice. The high CBD formulation is therefore useful as a means of reducing appetite in humans.

EXAMPLE 21

A specific chemovar (designated G9) produces two principal cannabinoids, THCV:THC in the ratio 85:15. This chemovar produces relatively little CBD and this exemplifies the extreme of the high THC:CBD ratios. THCV produces a more rapid analgesic effect than THC, with reduced potential for hangover. A pharmaceutical preparation prepared from this extract is therefore desirable for the treatment of opioid-resistant pain where a rapid onset of action is required. A sublingual spray formulation has the following formula.

CBME-G9 Extract Providing THCV 85 Parts THC 15 Parts

| Cremophor RH40 | 300 parts |
|---|---|
| α-tocopherol | 1 part |
| Ethanol BP to produce | 1,000 parts |

The ingredients are dissolved in the ethanol and dispensed in 10 ml quantities into a glass vial, closed with a pump action spray break-up button. Each 1 ml of product contains 100 mg of cannabinoid, and each actuation of the pump delivers 100 µl in a fine spray which is directed to the area of mucosae under the tongue.

This preparation is used as part of the treatment for patients suffering from migraine, cancer pain and multiple sclerosis.

EXAMPLE 22

A formulation as described in the preceding example is made up substituting CBME-G5 (high CBD). This spray can be used to prime patients by giving a dose of CBD 5-10 minutes before administration of the high THC/THCV formulation.

Proprietary two-compartment/double pressure buttons are available, and a composite package contains solution as described in this and the preceding example. The availability of the two sublingual solutions in a convenient package allows the patient to titrate the dose of either component to optimise the therapeutic effect required.

The antioxidant effect of CBD in vitro is demonstrated by the following assay levels after storage at 5±3° C. The data are reported as percentage of initial assay value.

TABLE 6

Stability Data for High THC and High CBD and Even Ratio CBD/THC, Pump Action Spray (PAS), and Sublingual Tablets.

| FORMU- LATION PASS | ASSAY VALUE AFTER ELAPSED TIME | | | |
|---|---|---|---|---|
| | 3 months (range) | | 6 months (range) | |
| | THC | CBD | THC | CBD |
| High THC | 98.2 (95.6–100.4) | | 95.6 (93.7–98.5) | |
| High CBD | | 100.6 (99.7–101.6) | | 101.0 (98.3–103.6) |
| Even ratio THC:CBD | 99.5 (98.3–101.5) | 101.2 (100.3–102.0) | 100.4 (99.3–102.8) | 104.5 (193.5–106.5) |
| SUBLINGUAL TABLETS STORED AT 5° C. | | | | |
| High THC (2 mg) | 98.4 | | | |
| High CBD (2 mg) | | 99.0 | | |
| Even ratio | 95.5 | 99.0 | | |

It is clear from the table above that CBD in this formulation has good stability, whereas THC is less stable. A preparation containing both CBD and THC in the concentrations which are of therapeutic interest appears to have a protective action and enhances the stability of the even ratio spray and tablet products.

The examples given above illustrate the teaching of the invention, and it will be clear to one skilled in the art that elements from the different formulations can be adapted to produce a wide range of formulations. These are suitable for treatment of a range of therapeutic indications. Elements may be taken from any of the above examples to produce a specific formulation with the desired speed of onset and duration of action within the limits described.

EXAMPLE 23

Cannabinoids are known to be useful in the treatment of inflammatory bowel disease. However, the amount of cannabinoid reaching the lower bowel (distal ileum and colon) is unknown. Enemas are suitable for local application of inflamed bowel. The following formulation is based on a foaming enema and provides a broad ratio combination of cannabinoids for local application.

| | |
|---|---|
| CBME-G1 providing THC | 4 mg |
| CBME-G5 providing CBD | 20 mg |
| Docusate sodium | 100 mg |
| Glycerol monostearate | 2.5 gm |
| Carboxymethylcellulose | 250 mg |
| Water | 250 ml |

The CBME extracts are dissolved in the ingredients and mixed in the order indicated above. A 50 ml quantity is dispensed into a compressible plastic container fitted with a 150 ml enema nozzle with a terminal bulb. Before use, the container is shaken vigorously to produce a foam. The foam is injected by the nozzle and the quantity of foam produced travels typically for 1-2 meters into the lower bowel. The foam is compressible and produces minimal discomfort to the patient compared with non-compressible enemas. The method of treatment can be combined with steroids given either systemically or as an enema for treatment of inflammatory bowel disease.

EXAMPLE 24

A product as described in Example 10 when placed in the maxillary fosse releases constituent into the buccal mucosae but also into the saliva present in the mouth. Coating the convex surface of the gel with a material that is less soluble than the substance of the gel will reduce the amount of constituent lost into the saliva and thereby increase the concentration in contact with the buccal mucosae. Formulations as described in Example 10 can be further modified in order to provide a gel in which a coating on the convex (proximal or inward facing surface) of the gel forms an integral part of the product. The added layer retards the dissolution of the gel and for convenience is referred to as a water insoluble layer (WIL). The WIL is a thermo setting gel which dispensed first into the mould at a temperature between 50-80° C. Whilst still warm the formulations described in Examples 10 or 11 are then dispensed in the manner and in the order described therein. Dispensing the molten mass while the WIL is still molten causes the WIL to be spread around the concave mould and results in a layer which is on the convex side of the contained, moulded gel.

When tested in the method described in Example 4, the distal portion of the gel dissolves leaving the WIL undissolved.

The WIL may be formed from the following composition in which the concentration of acacia gum in Example 11 is increased to give a more rigid, structural component of the gel.

| | |
|---|---|
| Glyceryl mono-oleate | 5 parts |
| Soya lecithin | 5 parts |
| Acacia gum | 30 parts |
| Tetrahydrocannabinol | 10 parts |
| α-tocopherol | 0.1 parts |
| Zylitol | 3 parts |
| Glycerol | 3 parts |
| Purified water to produce 100 parts | |

The ingredients are mixed as described in Example 11 and heated until dissolved. Aliquots are dispensed into moulds or as a sheet.

The similarity of the formulation in the WIL with the layer described in Example 11 results in a slight degree of mixing at the interface, and bonding of the components to give a coherent product.

The type of cannabinoid and proportion of cannabinoid, which are described in other examples, can be introduced into a multiple layer product as described in this example.

EXAMPLE 25

A water insoluble layer can also be formed on the gels by, for example, spraying a 5% solution of ethyl cellulose in ethanol on to the inner surface of the mould before introducing the first component described in Example 10. The alcoholic solution is sprayed through a mask, which protects the surface of the mould where it is intended to have an adherent layer of sealing film. The solvent is allowed to evaporate before introducing the gel as described in Example 10. This procedure has the added advantage, should it be needed, of reducing the bioburden on the inner surface of the mould. When mould composition is introduced into the mould it adheres strongly to the ethyl cellulose and forms the water insoluble layer. Where the medicament is formed by casting layers of material on a plane surface, a 5% solution of ethyl cellulose is sprayed onto the surface. After evaporation of solvent, the composite layer as described in Example 10 is formed thereon.

REFERENCES

Adams M. D. et al (1977)
A Cannabinoid with Cardiovascular Activity but no Overt Behavioural Effects
Experientia, 33, 1204-1205
Burstein S. and Raz A. (1972)
Inhibition of prostaglandin E2 biosynthesis by D1-tetrahydrocannabinol. Prostaglandins 2 :369-375.
Ed. Brown D. T, 207
Cannabis 'The Genus Cannabis'
Carlini E. A., Leiter J. R., Tannhauser M. and Berardi A. C. (1973) Cannabidiol and *Cannabis sativa* Extract Protect Mice and Rats Against Convulsive Agents
J. Pharm. Pharmacol 25, 664-665
Davis K H Jr., McDaniel I A Jr., et al
Some Smoking Characteristics of Marijuana Cigarettes.
The Cannabinoids: Chemical, Pharmacologic and Therapeutic Aspects
Academic Press, Inc. (1984)
De Meijer E. P. M. and Keizer L. C. P. (1996)
Patterns of diversity in *Cannabis. Genetic Resources and Crop Evolution,* 43, 41-52
Guy G W, Whittle B A and Grey M J
Dose dispensing Apparatus
GB Pat Application 25809.5, Oct. 20, 2000
Guy G W, Whittle B A and Grey M J
Secure dispensing of materials
GB Patent Application 25811.1, Oct. 20, 2000
Hampson A. J., Grimaldi M., Axelrod J. and Wink D. (1998)
Cannabidiol and (−) 9-Tetrahydrocannabinol are Neuroprotective Antioxidants
Proc. Nat. Acad. Sci. 95, 8268-8273
Hardy et al
Respiratory Medicine (1993) 87: 461-465
House of Lords Science and Technology Sub Committee report
The Development of Prescription Cannabis-Based Medicines (January 2001)
In-house Report GPA 002/000159
CBD Primary Screening Program (2000)
Iversen L. L.
The Science of Marijuana, Oxford University Press, 48-49 (2000)
Mechoulam R ed.
Cannabinoids as Therapeutic Agents, CRC Press, Boca Raton, Fla., New York (1976)
Merck Index, 12th Edition, (1996) #1792
Merck's Manual (1899), Part 1, pg 26.
Pate D. U.S. patent application Ser. No. 08/919317, 28 Aug. 1997
Pertwee R. G. (1998)
Advances in Cannabinoid Receptor Pharmacology in Cannabis
The Genus Cannabis (Ed. Brown D. T.) Harwood Publishers, 125-174
Petro D. J. (1980)
Marijuana as a Therapeutic Agent for Muscle Spasm or Spasticity
Psychosomatics 21(1), 81-85
Price M A P, and Notcutt W G
Cannabis in Pain Relief
In Cannabis: The Genus Cannabis (Ed Brown D T Harwood Publishers, 223-246
Raman A.
The Cannabis Plant: Cultivation and Processing for Use
In Cannabis: the genus *Cannabis,* 29 -54, Ed Brown D T
Ram and Sett (1982) Zeitschrift fur pflanzenphysiologie, 107(1), 85-89
Samuelsson G
Drugs of Natural Origin 155-160Swedish Pharmaceutical Press, Stockholm, Sweden,
Smiley K. A., Karber R. and Turkanis S. A. (1976)
Effect of Cannabinoids on the Perfussed Rat Heart Res. Comm. Chem. Pathol. Pharmacol, 14, 659-673
Tashkin D P, Shapiro B J, and Frank I M
Acute pulmonary and physiological effects of smoked marijuana and oral delta-9-THC in healthy young men N Eng J Med, 289, 336-341
Touitou E
U.S. Pat. No. 5,540,934 (Jul. 30, 1996)
Touitou E, Fabin B, Danny S and Almog S
Transdermal Delivery of Tetrahydrocannabinol Int. J. of Pharmaceutics (1988) 43: 9-15
Whittle B A and Guy G W
Formulations for sublingual delivery GB Patent Application 103638.3, Feb. 14, 2001
Zuardi A. W. and Guimares F. S. (1991)
Cannabidiol as an Anxiolytic and Antipsychotic in Cannabis: The Medicine Plant
McFarland & Co, London: 133-141
Equivalents All references disclosed herein are incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. A cannabis-based liquid pharmaceutical formulation for oro-pharangeal delivery comprising cannabidiol (CBD) and tetrahydrocannabinol (THC), formulated as a pump-action spray in a pre-defined ratio by weight, a solvent and a co-solvent, wherein the CBD and THC are provided as carbon dioxide extracts obtained from two or more different Cannabis chemovars from which non-specific lipid-soluble material has been removed, and in which the Cannabis chemovars include a first chemovar in which THC is more than 95% of the total cannabinoid and a second chemovar in which CBD is more than 90% of the total cannabinoid, and wherein the CBD and THC are present in the formulation in an amount of at least 1.0 mg per 0.1 ml, and wherein the solvent is ethanol, and the co-solvent is a polyoxyethylene castor oil derivative, propylene glycol or glycerol.

2. A pharmaceutical formulation according to claim 1 which comprises both the cannabinoids cannabidiol (CBD) and tetrahydrocannabinol (THC) in approximately equal amounts by weight.

3. A pharmaceutical formulation according to claim 1 which comprises both the cannabinoids cannabidiol (CBD) and tetrahydrocannabinol (THC), wherein the THC is present in an amount by weight which is greater than the amount by weight of CBD.

4. A pharmaceutical formulation according to claim 1 which comprises both the cannabinoids cannabidiol (CBD) and tetrahydrocannabinol (THC), wherein the CBD is present in an amount by weight which is greater than the amount by weight of THC.

5. A pharmaceutical formulation according to claim 1 wherein the formulation is in a liquid dosage form producing particles having a mean aerodynamic particle size between 15 and 45 microns.

6. A pharmaceutical formulation according to claim 5 wherein the particle size is between 20 and 40 microns.

7. A pharmaceutical formulation according to claim 5 wherein the average particle size is about 33 microns.

8. A pharmaceutical formulation according to claim 4 wherein the ratio by weight of CBD to THC is in the range from 5:1 to 3:1.

9. A pharmaceutical formulation according to claim 1 which is substantially free of cannabinoids other than CBD and THC.

10. A pharmaceutical formulation according to claim 1 which is substantially free of other cannabinoids found in Cannabis sp.

11. A pharmaceutical formulation according to claim 1 which further comprises one or more other cannabinoids.

12. A pharmaceutical formulation according to claim 11 wherein the one or more other cannabinoids are tetrahydrocannabivarin (THCV) and/or cannabidivarin (CBDV).

13. A pharmaceutical formulation according to claim 1 wherein the CBD and THC are derived from the extracts from two or more Cannabis chemovars, said extracts from two or more Cannabis chemovars comprising all the naturally occurring cannabinoids in said Cannabis chemovars.

14. A pharmaceutical formulation according to claim 13 wherein the Cannabis chemovars are selected from Cannabis sativa, Cannabis indica, a genetic cross between them, a self-cross or a hybrid thereof.

15. A pharmaceutical formulation according to claim 14 wherein the Cannabis chemovars are Cannabis sativa, sub-species indica and is selected from var. indica and var. kafiristanica.

16. A pharmaceutical formulation as claimed in claim 13, wherein in the final formulation the amount of CBD is greater than the amount of THC by weight.

17. A pharmaceutical formulation according to claim 11 wherein said extract is prepared by supercritical or subcritical fluid extraction of dried Cannabis plant.

18. A method of preparing a Cannabis-based pharmaceutical formulation which comprises CBD and THC in a pre-defined ratio by weight which method comprises the steps of:
   a) providing two or more different Cannabis plant chemovars for which the amount of CBD and THC by weight is known, and wherein THC is more than 95% of the total cannabinoid in the first chemovar and CBD is more than 90% of the total cannabinoid in the second chemovar;
   b) preparing a carbon dioxide extract of said two or more Cannabis chemovars;
   c) removing non-specific lipid-soluble material from the extract;
   d) formulating a material from said extract or extracts prepared in step (c) which exhibits said pre-defined ratio by weight of CBD to THC; and
   e) further formulating the product of step (d) into a liquid pharmaceutical formulation for oropharangeal delivery with a pharmaceutically acceptable carrier or diluent, a solvent and a co-solvent; wherein the CBD and THC are present in the formulation in an amount of at least 1.0 mg per 0.1 ml; wherein the solvent is ethanol, and the co-solvent is a polyoxyethylene castor oil derivative, propylene glycol or glycerol; and wherein the liquid pharmaceutical formulation is formulated as a pump-action spray.

19. A method according to claim 18 wherein the pharmaceutically acceptable carrier or diluent is a liquid and the formulation produces particles having a mean aerodynamic particle size between 15 and 45 microns.

20. A method according to claim 19 wherein the particle size is between 20 and 40 microns.

21. A method according to claim 19 wherein the average particle size is about 33 microns.

22. A method according to claim 18 wherein the extract of step (b) is prepared using extraction with liquid carbon dioxide under pressure.

23. A method according to claim 18 wherein prior to extraction said dried Cannabis is heated to a temperature of from about 60° C. to about 225° C. to decarboxylate the acid form of any cannabinoids present in the extract.

24. A method according to claim 18 which comprises extracting said two or more Cannabis chemovars with supercritical or subcritical CO2.

25. A method according to claim 24 wherein after extraction with said supercritical or subcritical CO2 said extract is subjected to "winterisation" to remove waxes from the extract in step (c).

26. A pharmaceutical formulation according to claim 13 which is a botanical drug product prepared from a botanical drug substance.

27. A pharmaceutical formulation according to claim 13 wherein each extract is derived from a specific chemovar.

28. A pharmaceutical formulation according to claim 26 wherein the botanical drug substance has an HPLC profile with THC, CBD and CBN having retention times of 9.6-10.6 minutes, 5.4-5.9 minutes and 7.9-8.7 minutes respectively.

29. The method according to claim 18 wherein the formulation comprises approximately equal amounts of CBD and THC by weight.

30. The method according to claim 18 wherein the amount by weight of THC in said formulation is greater than the amount by weight of CBD.

31. A method according to claim 18 wherein the pharmaceutical formulation comprises both the cannabinoids cannabidiol (CBD) and tetrahydrocannabinol (THC), wherein the CBD is present in an amount by weight which is greater than the amount by weight of THC.

32. A method according to claim 18 wherein said pre-defined ratio by weight of CBD to THC is in the range from about 5:1 to 3:1.

33. A method according to claim 18 wherein said formulation is formulated for delivery sub-lingually, buccally, or orally.

34. A method according to claim 18 wherein said formulation is formulated to deliver CBD prior to delivery of THC and/or to provide a controlled release formulation.

* * * * *